(12) United States Patent
Cleek et al.

(10) Patent No.: US 8,591,932 B2
(45) Date of Patent: Nov. 26, 2013

(54) HEPARIN ENTITIES AND METHODS OF USE

(75) Inventors: Robert L. Cleek, Flagstaff, AZ (US);
Paul D Drumheller, Flagstaff, AZ (US);
Mei Li, Flagstaff, AZ (US); Nora Mardirosian, Bellemont, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 507 days.

(21) Appl. No.: 12/561,927

(22) Filed: Sep. 17, 2009

(65) Prior Publication Data

US 2011/0064781 A1    Mar. 17, 2011

(51) Int. Cl.
*A61F 2/02*    (2006.01)
(52) U.S. Cl.
USPC .......................................................... 424/423
(58) Field of Classification Search
None
See application file for complete search history.

(56) References Cited

U.S. PATENT DOCUMENTS

| | | |
|---|---|---|
| 3,953,566 A | 4/1976 | Gore |
| 4,187,390 A | 2/1980 | Gore |
| 4,326,532 A | 4/1982 | Hammar |
| 4,329,383 A | 5/1982 | Joh |
| 4,415,490 A | 11/1983 | Joh |
| 4,526,714 A | 7/1985 | Feijen et al. |
| 4,600,652 A | 7/1986 | Solomon et al. |
| 4,613,665 A | 9/1986 | Larm |
| 4,678,671 A | 7/1987 | Feijen et al. |
| 4,745,180 A | 5/1988 | Moreland et al. |
| 4,810,784 A | 3/1989 | Larm |
| 4,944,767 A | 7/1990 | Barbucci et al. |
| 5,032,666 A | 7/1991 | Hu et al. |
| 5,130,143 A | 7/1992 | Strickland et al. |
| 5,213,898 A | 5/1993 | Larm et al. |
| 5,308,617 A | 5/1994 | Halluin |
| 5,417,969 A | 5/1995 | Hsu et al. |
| 5,476,666 A | 12/1995 | Rhee et al. |
| 5,510,418 A | 4/1996 | Rhee et al. |
| 5,527,524 A | 6/1996 | Tomalia et al. |
| 5,529,986 A | 6/1996 | Larsson et al. |
| 5,532,311 A | 7/1996 | Sirvio et al. |
| 5,583,213 A | 12/1996 | Yafuso et al. |
| 5,876,433 A | 3/1999 | Lunn |
| 5,897,955 A | 4/1999 | Drumheller |
| 5,914,182 A | 6/1999 | Drumheller |
| 5,916,585 A | 6/1999 | Cook et al. |
| 5,922,690 A | 7/1999 | Van Gorp et al. |
| 6,096,525 A | 8/2000 | Patnaik |
| 6,120,536 A | 9/2000 | Ding et al. |

(Continued)

FOREIGN PATENT DOCUMENTS

| | | |
|---|---|---|
| EP | 0086186 | 2/1983 |
| EP | 0086187 | 2/1983 |

(Continued)

OTHER PUBLICATIONS

"Heparin", Wikipedia.com, 2012.*

(Continued)

*Primary Examiner* — Carlos Azpuru
(74) *Attorney, Agent, or Firm* — Carol A. Lewis White

(57) ABSTRACT

The present invention relates to immobilized biologically active entities that retain a significant biological activity following manipulation. The invention also comprises a medical substrate comprising a heparin entity bound onto a substrate via at least one heparin molecule, wherein said bound heparin entity is heparinase-1 sensitive.

21 Claims, 9 Drawing Sheets

(56) References Cited

U.S. PATENT DOCUMENTS

| | | | |
|---|---|---|---|
| 6,361,819 | B1 | 3/2002 | Tedeschi et al. |
| 6,406,687 | B1 | 6/2002 | Luthra et al. |
| 6,440,947 | B1 | 8/2002 | Barron et al. |
| 6,461,665 | B1 | 10/2002 | Scholander |
| 6,642,242 | B2 | 11/2003 | Collis et al. |
| 6,787,179 | B2 | 9/2004 | Timm et al. |
| 6,887,249 | B1 | 5/2005 | Houser et al. |
| 7,045,585 | B2 | 5/2006 | Berry et al. |
| 7,641,682 | B2 | 1/2010 | Palmaz et al. |
| 7,736,687 | B2 | 6/2010 | Sims et al. |
| 2001/0036932 | A1 | 11/2001 | Cardin et al. |
| 2001/0044654 | A1 | 11/2001 | Chen et al. |
| 2002/0146414 | A1 | 10/2002 | Sakiyama-Elbert |
| 2003/0135195 | A1 | 7/2003 | Jimenez et al. |
| 2005/0059068 | A1 | 3/2005 | Huang et al. |
| 2005/0220839 | A1 | 10/2005 | DeWitt et al. |
| 2005/0232971 | A1 | 10/2005 | Hossainy et al. |
| 2006/0204533 | A1 | 9/2006 | Hsu et al. |
| 2007/0098708 | A1 | 5/2007 | Myette |
| 2007/0212388 | A1 | 9/2007 | Patravale |
| 2007/0264302 | A1 | 11/2007 | Cleek et al. |
| 2007/0264308 | A1 | 11/2007 | Cleek et al. |
| 2008/0267903 | A1 | 10/2008 | Uchegbu et al. |
| 2008/0279909 | A1 | 11/2008 | Cleek et al. |
| 2009/0274737 | A1 | 11/2009 | Borck |

FOREIGN PATENT DOCUMENTS

| | | |
|---|---|---|
| EP | 0495820 | 7/1992 |
| EP | 923 953 | 6/1999 |
| EP | 0956870 | 11/1999 |
| EP | 1559434 | 8/2005 |
| EP | 1916260 | 4/2008 |
| WO | 87/07156 | 12/1987 |
| WO | 93/05793 | 4/1993 |
| WO | 97/07834 | 3/1997 |
| WO | 98/08552 | 3/1998 |
| WO | 00/01843 | 1/2000 |
| WO | 01/41827 | 6/2001 |
| WO | 01/87375 | 11/2001 |
| WO | 03/057270 | 7/2003 |
| WO | 2005/018552 | 3/2005 |
| WO | WO 2005/018552 | 3/2005 |
| WO | 2007/133699 | 11/2007 |
| WO | 2008/063157 | 5/2008 |
| WO | 2010/029189 | 3/2010 |

OTHER PUBLICATIONS

Choay J. Biologic studies on chemically synthesized pentasaccharide and tetrasaccharide fragments. Seminars in Thrombosis and Hemostasis 1985; 11:81-85.

Freudenberg U, Hermann A, Welzel P et al. A star-PEG-heparin hydrogel platform to aid cell replacement therapies for neurodegenerative diseases. Biomaterials 2009; 30: 5049-5060.

Griffith M. Heparin-catalyzed inhibitor/protease reactions: Kinetic evidence for a common mechanism of action of heparin. Proc. Natl. Acad. Sci. 1983: 80:5460-5464.

Horner A. Molecular-size-dependent variations in the proportions of chains with high binding affinities for antithrombin in rat skin heparin proteoglycans. Biochem. J. 1989; 262:953-958.

Klement P, Du Y, Berry L et al. Blood-compatibile biomaterials by surface coating with a novel antithrombin-heparin covalent complex. Biomaterials 2002; 23:527-535.

Lam L, Silbert J, Rosenberg R. The separation of active and inactive forms of heparin. Biochem. Biophys. Res. Comm. 1976; 69:570-577.

Larsen, M.L. et al., Assay of Plasma Heparin Using Thrombin and the Chromogenic Substrate H-D-Phe-Pip-Arg-pNA (S-2238). Thromb Res 1978; 13:285-288.

Macintosh F. A colorimetric method for the standardization of heparin preparations. Biochem. 1941; 35:776-782.

Mulloy B, Forster, M. Conformation and dynamics of heparin and heparan sulfate. Glycobiology 2000; 10:1147-1156.

Oliveira G, Carvalho L, Silva M. Properties of carbodiimide treated heparin. Biomaterials 2003; 24: 4777-4783.

Pasche B, Elgue G, Olsson P et al. Binding of antithrombin to immobilized heparin under varying flow conditions. Artif. Organs 1991;15:481-491.

Rosenberg R, Jordan R, Favreau L et al. Highly active heparin species with multiple binding sites for antithrombin. Biochem. Biophys. Res. Comm. 1979; 86:1319-1324.

Tanzi M. Bioactive technologies for hemocompatibility. Expert Rev. Med. Devices 2005; 2:473-492.

Yamaguchi N, Kiick K. Polysaccharide-poly(ethylene glycol) star copolymer as a scaffold for the production of bioactive hydrogels. Biomacromolecules 2005; 6;1921-1930.

Kadir,A. et al. Saccaride sensing using gold and silver nanoparticles—A review. Journal of Fluorescence. 2004;14:391-400.

Linhardt RJ, Turnbull JE, Wang HM, Loganathan D, Gallagher T. (1990)Examination of the Substrate Specificity of Heparin and Heparan Sulfate Lyases. Biochemistry, vol. 29, p. 2611-2617.

Hinrichs WLJ, ten Hoopen HWM, Wissink MJB, Engbers GHM, Feijen J. (1997) Design of a new type of coating for the controlled release of heparin. Journal of Controlled Release, vol. 45, p. 163-176.

Hardhammar, PA, van Beusekom HMM, Emanuelsson HU, et al. Reduction in Thrombotic Events With Heparin-Coated Palmaz-Schatz Stents in Normal Porcine Coronary Arteries. Circulation 1996; v93 n2:423-430.

Lin Ph, Chronos NA, Marijianowski MM, Chen C, et al. Heparin-coated Balloon-expandable Stent Reduces Intimal Hyperplasia in the Iliac Artery in Baboons. J Vasc Interv Radiol 2003; 14:603-611.

Gavalas VG, Chaniotakis NA, Gibson TD. Improved operational stability of biosensors based on enzyme-polyelectrolyte complex adsorbed into a porous carbon electrode. Biosensors & Bioelectronics 1998;13:1205-1211.

Gibson TD, Pierce BLJ, Parker SM. Stabilisation of the Biological component of Biosensors. Biosensors for Food Analysis 1998; 46-53.

Rocchietti S, Ubiali D, Terreni M, et al. Immobilization and Stabilization of Recombinant Mulitmeric Uridine and Purine Nucleoside Phosphorylases from *Bacillus subtilis*. Biomacromolecules 2004; 5:2195-2200.

Lin PH, Chronos NA, Marijianowski MM, Chen C, Bush RL, Conklin B, Lumsden AB, Hanson Sr. Heparin-coated Balloon-expandable Stent Reduces Intimal Hyperplasia in the Iliac Artery in Baboons. Journal of Vascular and Interventional Radiology 2003; vol. 14, No. 5, p. 603-611.

Lin PH, Chen C, Bush RL, Yao Q, Lumsden AB, Hanson SR. Small-caliber heparin-coated ePTFE grafts reduce platelet deposition and neointimal hyperplasia in a baboon model. Journal of Vascular Surgery 2004; vol. 39, No. 6, p. 1322-1328.

Lin Ph, Bush RL, Yao Q, Lumsden AB, Chen C. Evaluation of Platelet Deposition and Neointimal Hyperplasia of Heparin-Coated Small-Caliber ePTFE Grafts in a Canine Femoral Artery Bypass Model. Journal of Surgical Research 2004; vol. 118, No. 1, p. 45-52.

Letourneur D, Machy D, Pellé A, Marcon-Bachari E, D'Angelo G, Vogel M, Chaubet F, Michel JB. Heparin and non-heparin-like dextrans differentially modulate endothelial cell proliferation: in vitro evaluation with soluble and crosslinked polysaccharide matrices. Journal of Biomedical Materials Research 2002; vol. 60, No. 1, p. 94-100.

Park KD, Kim YS, Han DK, Kim YH, Lee EHB, Suh H, Choi KS. Bacterial adhesion on PEG modified polyurethane surfaces. Biomaterials 1998; vol. 19, No. 7-9, p. 851-859.

Salu KJ, Bosmans JM, Bult H, Vrints CJ. Drug-eluting stents: a new treatment in the prevention of restenosis Part I: experimental studies. Acta Cardiologica 2004; vol. 59, No. 1, p. 51-61.

Leclerc G. Drug Delivery from PC-Coated Stents. Japanese Journal of Interventional Cardiology 2001; vol. 16, No. Suppl. 1, p. 107.

Hellstrom WJG, Hyun JS, Human L, Sanabria JA, Bivalacqua TJ, Leungwattanakij S. Antimicrobial activity of antibiotic-soaked, Resist™-coated Bioflex®. International Journal of Impotence Research 2003; vol. 15, No. 1, p. 18-21.

\* cited by examiner

FIGURE 3 A-B
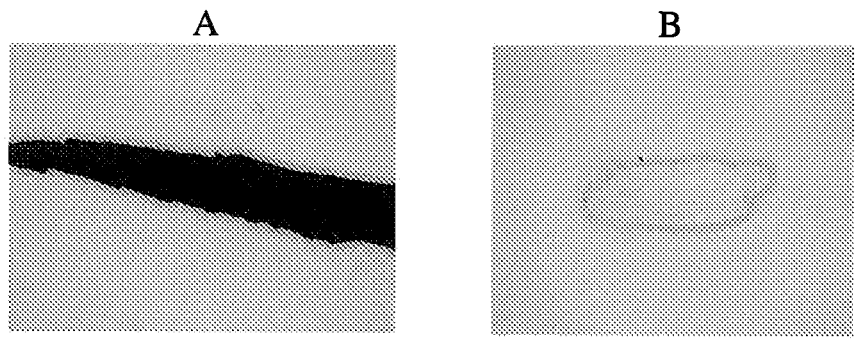
FIGURE 3 C
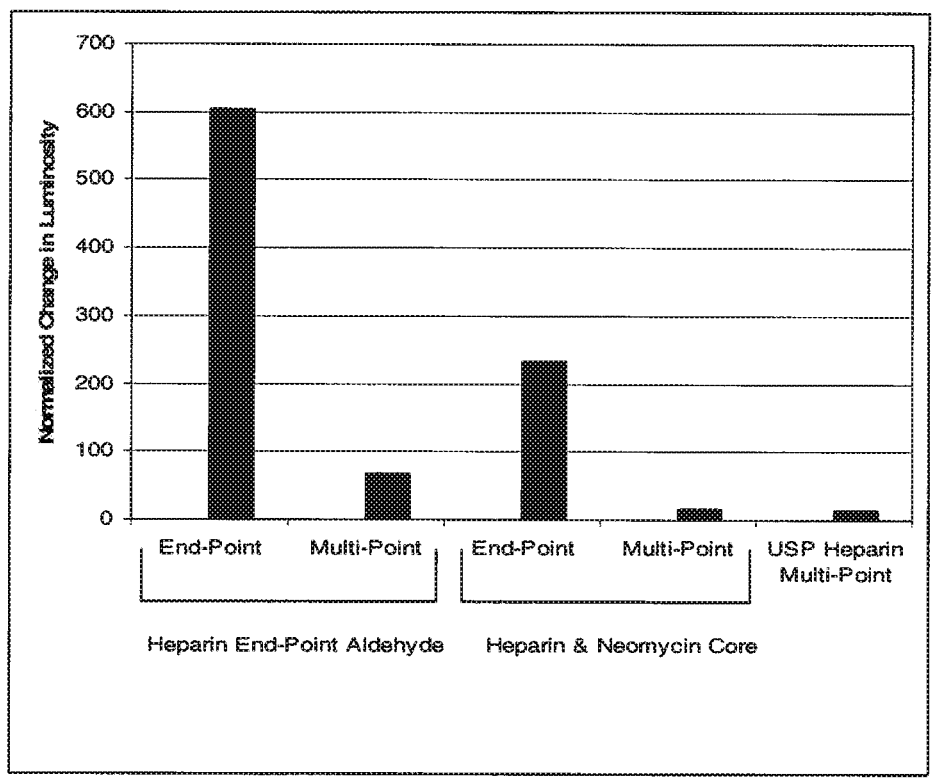

FIGURES 4A-C
A  B  C
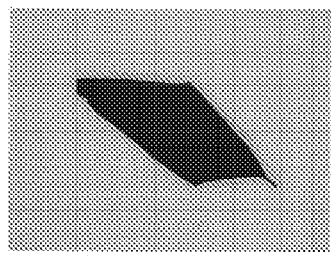 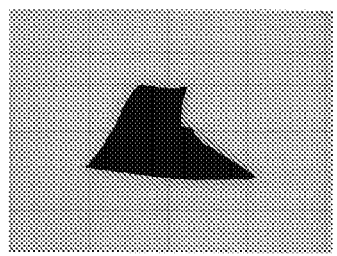 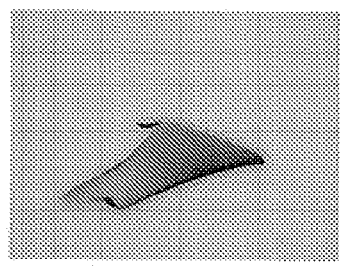
FIGURES 4 D-E
D  E
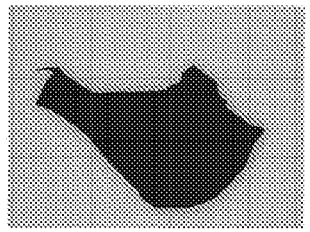 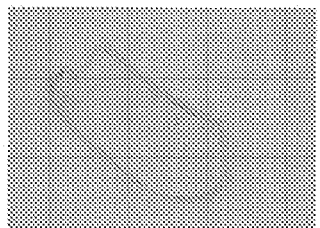

HEPARIN ENTITIES AND METHODS OF USE

FIELD OF THE INVENTION

The present invention relates to medical substrates having immobilized biologically active entities that maintain their biological activity after sterilization. Specifically the present invention relates to new heparin entities and their method of use.

BACKGROUND OF THE INVENTION

Medical devices which serve as substitute blood vessels, synthetic and intraocular lenses, electrodes, catheters and the like in and on the body or as extracorporeal devices intended to be connected to the body to assist in surgery or dialysis are well known. However, the use of biomaterials in medical devices can stimulate adverse body responses, including rapid thrombogenic action. Various plasma proteins play a role in initiating platelet and fibrin deposition on biomaterial surfaces. These actions lead to vascular constriction that hinder blood flow, and the inflammatory reaction that follows can lead to the loss of function of the medical device. Biologically active entities that reduce or inhibit thrombus formation on the surface of a biomaterial and/or covering material are of particular interest for blood contacting devices. Glycosaminoglycans are generally preferred anti-thrombotic agents; with heparin, heparin analogs, and derivatives being particularly preferred.

Immobilization of glycosaminoglycans, such as heparin, to biomaterials has been researched extensively to improve bio- and hemocompatibility. The mechanism responsible for reducing thrombogenicity of a heparinzed material is believed to reside in the ability of heparin to speed up the inactivation of serine proteases (blood coagulation enzymes) by anti-thrombin III (ATIII). In the process, ATIII forms a complex with a well defined pentasaccharide sequence in heparin, undergoing a conformational change and thus enhancing the ability of ATIII to form a covalent bond with the active sites of serine proteases, such as thrombin. The formed serine protease-ATIII complex is then released from the heparin, leaving said heparin behind for subsequent rounds of inactivation via a catalytic process.

Immobilization of biologically active entities, such as heparin, on biomaterials in a biologically active form involves an appreciation of the respective chemistries of the entity and the biomaterial. In the field of medical devices, ceramic, polymeric, and/or metallic materials are common biomaterials. These materials can be used for implantable devices, diagnostic devices or extracorporeal devices. Modification of the chemical composition of a biomaterial is often required to immobilize a biologically active entity thereon. This modification is usually accomplished by treating surfaces of the biomaterial to generate a population of chemically reactive moieties or groups, followed by immobilization of the biologically active entity with an appropriate protocol. With other biomaterials, surfaces of a biomaterial are covered, or coated, with a material having reactive chemical groups incorporated therein. Biologically active entities are then immobilized on the biomaterial through the reactive chemical groups of the covering material. A variety of schemes for covering, or coating, biomaterials have been described. Representative examples of biologically active entities immobilized to a biomaterial with a covering, or coating, are described in U.S. Pat. Nos. 4,810,784; 5,213,898; 5,897,955; 5,914,182; 5,916,585; and 6,461,665.

When biologically active compounds, compositions, or entities are immobilized, the biological activity of these "biologics" can be negatively impacted by the process of immobilization. The biological activity of many biologics is dependent on the conformation and structure (i.e., primary, secondary, tertiary, etc.) of the biologic in its immobilized state. In addition to a carefully selected immobilization process, chemical alterations to the biologic may be required for the biologic to be incorporated into the covering material with a conformation and structure that renders the biologic sufficiently active to perform its intended function.

Despite an optimized covering and immobilization scheme, additional processing, such as sterilization, can degrade the biological activity of the immobilized biologic. For implantable medical devices, sterilization is required prior to use. Sterilization may also be required for in vitro diagnostic devices having sensitivity to contaminants. Sterilization of such devices often requires exposure of the devices to elevated temperature, pressure, and humidity, often for several cycles. In some instances, antimicrobial sterilants, such as ethylene oxide gas (EtO) or vapor hydrogen peroxide, are included in the sterilization process. In addition to sterilization, mechanical compaction and expansion, or long-term storage of an immobilized biologic can degrade the activity of the biologic.

There exists a need for medical devices having biologically active entities immobilized thereon that can be subjected to sterilization, mechanical compaction and expansion, and/or storage without significant loss of biological activity. Such a medical device would have biologically compatible compositions or compounds included with the immobilized biological entities that serve to minimize degradation of the biological activity of the entities during sterilization, mechanical compaction and expansion, and/or storage. In some instances, the additional biologically compatible compositions or compounds would increase the biological activity of some biologically active entities following a sterilization procedure.

SUMMARY OF THE INVENTION

Thus, the present invention comprises medical substrates comprising heparin entities immobilized onto a substrate. The heparin entities of the invention retain significant biological activity following immobilization, sterilization, mechanical compaction and expansion, and/or storage, as compared to other coated medical substrates.

One embodiment of the invention comprises a medical substrate comprising a heparin entity bound onto a substrate via at least one heparin molecule, wherein said bound heparin entity is heparinase sensitive. In another embodiment, said substrate is selected from the group consisting of polyethylene, polyurethane, silicone, polyamide-containing polymers, polypropylene, polytetrafluoroethylene, expanded-polytetrafluoroethylene, fluoropolymers, polyolefins, ceramics, and biocompatible metals. In another embodiment, said substrate is expanded-polytetrafluoroethylene. In another embodiment, said biocompatible metal is a nickel-titanium alloy, such as Nitinol. In another embodiment, said substrate is a component of a medical device. In another embodiment, said medical device is selected from the group consisting of grafts, vascular grafts, stents, stent-grafts, bifurcated grafts, bifurcated stents, bifurcated stent-grafts, patches, plugs, drug delivery devices, catheters, cardiac pacemaker leads, balloons, and indwelling vascular filters. In another embodiment, after heparinase treatment, heparin, or fragments thereof, will not be detected on said substrate.

Another embodiment of the invention comprises a heparin entity comprising at least one heparin molecule and at least one core molecule such that when said heparin entity is bound onto a substrate via a least one heparin molecule, said heparin entity is heparinase sensitive. In one embodiment, said core molecule is selected from the group consisting of proteins (including polypeptides), hydrocarbons, aminoglycosides, polysaccharides and polymers. In another embodiment, said heparin entity is bound onto a substrate via at least one heparin molecule and wherein said bound heparin molecule is attached to said substrate via end point attachment. In another embodiment, said heparin entity is bound onto a substrate via at least one heparin molecule and wherein said bound heparin molecule is attached to said substrate via loop attachment.

Another embodiment of the invention comprises an ATIII binding entity comprising a core molecule, at least one polysaccharide chain attached to the core molecule, and at least one free terminal aldehyde moiety on the polysaccharide chain. In one embodiment, said polysaccharide chain is heparin or a heparin fragment. In another embodiment, said core molecule is selected from the group consisting of a protein (including polypeptides), a hydrocarbon, an aminoglycoside, a polysaccharide and a polymer. In another embodiment, said substrate is selected from the group consisting of polyethylene, polyurethane, silicone, polyamide-containing polymers, polypropylene, polytetrafluoroethylene, expanded-polytetrafluoroethylene, fluoropolymers, polyolefins, ceramics, and biocompatible metals. In another embodiment, said ATIII binding entity is bound onto a substrate via end-point attachment or loop attachment. In another embodiment, said substrate is a component of a medical device.

Another embodiment of the invention comprises a method of determining the structure of a heparin entity bonded to a substrate, comprising the steps of providing a substrate comprising a heparin entity, depolymerizing the heparin entity to generate a mixture of soluble heparin fragments, detecting each soluble heparin fragment in said mixture using column chromatography, determining the identity of each detected heparin fragment from the above step, and deriving the structure of the heparin entity from the identities of the detected heparin fragments. In one embodiment, said depolymerizing is by heparinase depolymerization. In another embodiment, said column chromatography is strong anion exchange high performance liquid chromatography (SAX-HPLC).

Another embodiment of the invention comprises a system for determining the structure of a heparin entity bonded to a substrate, comprising a depolymerization solution, a labeling reagent solution, and a detector. In another embodiment, said depolymerization solution comprises heparinase. In another embodiment, said labeling reagent solution comprises toluidine blue and terbium tris(4-methylthio)benzoate. In another embodiment, said detector comprises SAX-HPLC, an epifluorescent microscope, and an absorption spectroscope.

BRIEF DESCRIPTION OF THE DRAWINGS

FIGS. 3 A and B depict light micrographs of heparin entities comprising free terminal aldehydes immobilized onto an ePTFE substrate by a single end-point attachment method before (3A) and after (3B) treatment with heparinase-1 and stained with toluidine blue. The absence of coloration in Figure B as compared to A, demonstrates that heparin entities comprising free terminal aldehydes immobilized onto an ePTFE substrate by a single end-point attachment method is essentially depolymerized from the surface after heparinase-1 treatment.

FIG. 3 C depicts the normalized change in luminosity before and after treatment with heparinase-1 for heparin immobilized through end-point aldehyde and multi-point attachment, heparin entities comprising a neomycin core immobilized through end-point and multi-point attachment through at least one heparin molecule, and USP heparin immobilized through multi-point attachment. The low normalized change in luminosity values for the heparin end-point aldehyde, heparin entity comprising heparin and neomycin core with end-point aldehyde, and USP heparin, all multi-point attached to the substrate, indicated that the surfaces are not heparinase-1 sensitive and still have substantial heparin on the surface.

FIGS. 4 A-C depicts light micrographs of heparin entities comprising heparin and an EDA core immobilized onto an ePTFE substrate by a single end-point attachment method before (4A and 4B) and after (4C) treatment with heparinase-1 and stained with toluidine blue. The stained samples demonstrate the presence of the heparin entity. Samples 4B and 4C were subjected to a round of sterilization and rinsed only with DI water post sterilization. The coloration of FIG. 4C after sterilization and heparinase-1 treatment indicates that heparinase-1 did not recognize heparin entities on the surface.

FIGS. 4 D and E depict light micrographs of heparin entities comprising heparin and an EDA core immobilized onto an ePTFE substrate by a single end-point attachment method before (4D) and after (4E) treatment with heparinase-1 and stained with toluidine blue. These samples where subjected to a round of sterilization and rinsed with DI water and boric acid post sterilization. The lack coloration of FIG. 4E after sterilization indicates that heparinase-1 did recognize heparin entities on the surface and depolymerized them.

DETAILED DESCRIPTION

Figure 1:
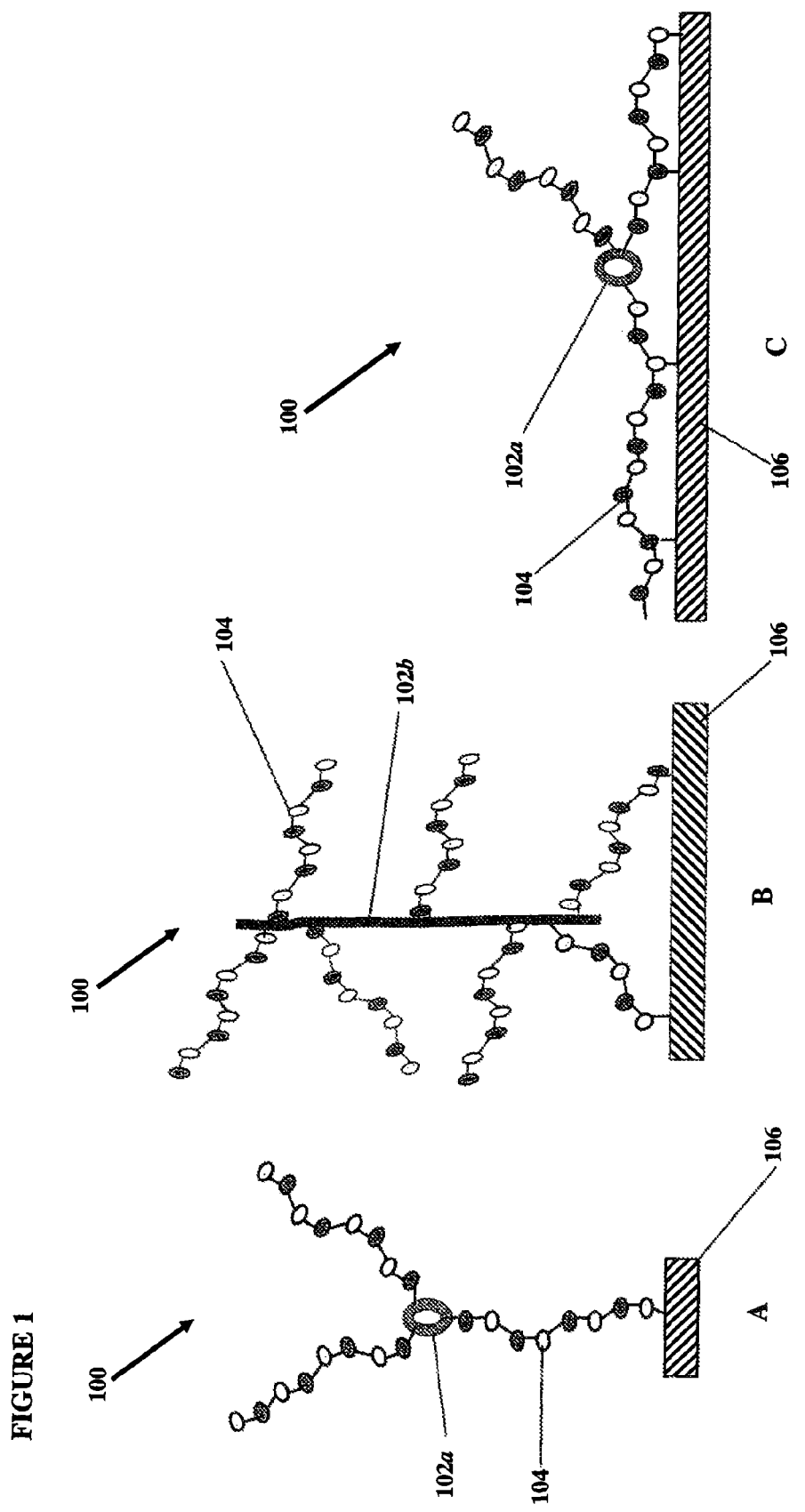
FIG. 1 depicts several heparin entities of the invention and types of attachment of said heparin entities to a substrate.

The present invention comprises medical substrates comprising heparin entities immobilized onto a substrate. The heparin entities of the invention retain significant biological activity following immobilization and sterilization as compared to other coated medical substrates.

In the context of this disclosure, a number of terms are used. The following definitions are provided. As used herein and in the appended claims, the singular forms "a", "an", and "the" include plural reference unless the context clearly dictates otherwise.

As used herein the term "heparin entity" means heparin molecules covalently attached to a core molecule. Said heparin molecules can be attached to the core molecule by end point attachment (as described below and as essentially described in U.S. Pat. No. 4,613,665, incorporated by reference herein for all purposes) or other methods known in the art (see e.g. G T Hermanson, Bioconjugate Techniques, Academic Press, 1996; H G Garg et al., Chemistry and Biology of Heparin and Heparan Sulfate, Elsevier, 2005.)

As used herein the term "core molecule" means a polyfunctional molecule to which heparin is attached. For the purposes of this invention, said core molecule and a substrate are not the same, although a core molecule and a substrate can be made from the same material.

As used herein, the term "substantially pure" means, an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 to about 90 percent of all macromolecular species present in the composition. Most preferably, the object species is purified to essential homogeneity (contaminant species cannot be detected in the composition by conventional detection methods) wherein the composition consists essentially of a single macromolecular species.

As used herein, the term "heparinase" means any enzymatic reaction that depolymerizes (e.g. digests) heparin. Examples of heparinase include, but are not limited to, heparinase-1, heparinase-2, heparinase-3, heparanase, exosulphatases, bacterial exoenzymes, and glycosidases that can depolymerize heparin.

As used herein the term "heparinase sensitive" means that after treatment of a substrate comprising heparin entities with heparinase and staining said substrate with toluidine blue, the substrate will not be visibly stained (essentially as depicted in FIG. 3 B and FIG. 4 E). The term also means that an insignificant amount of toluidine blue will bind to residual heparin, or fragments thereof, and a reading from a detector that can measure the amount of toluidine blue (or other labels) on a substrate, such as a spectrophotometer, luminometer, densitometer, liquid scintillation counter, gamma counter, or the like, will be about background levels, or be insignificantly different from background levels when compared to a substrate without heparin entities and stained with toluidine blue, or be below the sensitivity of said detectors when compared to a substrate comprising heparin entities and stained with toluidine blue without heparinase treatment. The term also means that a label that binds to heparin, or fragments thereof, will not detect a substantial amount of heparin, or fragments thereof, after treatment of a substrate comprising heparin entities with heparinase.

As used herein the terms "bound," "attached," and "conjugate," and their derivatives, when referring to heparin entities and/or heparin means covalently bound, unless specified otherwise.

Referring to FIGS. 1A-C, one embodiment of the invention comprises a medical substrate comprising a heparin entity 100 bound onto a substrate 106 via at least one heparin molecule 104, wherein said bound heparin entity is heparinase sensitive. Suitable substrate materials for immobilizing or binding said heparin entities comprise polymers such as, but not limited to, polyamides, polycarbonates, polyesters, polyolefins, polystyrene, polyurethane, poly(ether urethane), polyvinyl chlorides, silicones, polyethylenes, polypropylenes, polyisoprenes, polytetrafluoroethylenes, and expanded-polytetrafluoroethylenes (ePTFE, as described in U.S. Pat. No. 4,187,390). In one embodiment, expanded, or porous, polytetrafluoroethylene (ePTFE) is the substrate.

Additional substrates include, but are not limited to, hydrophobic substrates such as polytetrafluoroethylene, expanded polytetrafluoroethylene, porous polytetrafluoroethylene, fluorinated ethylene propylene, hexafluoropropylene, polyethylene, polypropylene, nylon, polyethyleneterephthalate, polyurethane, rubber, silicone rubber, polystyrene, polysulfone, polyester, polyhydroxyacids, polycarbonate, polyimide, polyamide, polyamino acids, regenerated cellulose, and proteins, such as silk, wool, and leather. Methods of making porous polytetrafluoroethylene materials are described in U.S. Pat. Nos. 3,953,566 and 4,187,390, each of which is incorporated herein by reference. In another embodiment, said ePTFE may be impregnated, filled, imbibed or coated with at least one chemical compound known to cause a bioactive response. Compounds that cause a bioactive response comprise anti-microbials (e.g. anti-bacterials and anti-virals), anti-inflammatories (e.g. dexamethasone and prednisone), anti-proliferatives (e.g. taxol, paclitaxel and docetaxel) and anti-coagulating agents (e.g. abciximab, eptifibatide and tirofibran). In one embodiment, said anti-inflammatory is a steroid. In another embodiment, said steroid is dexamethasone. Methods of coating substrates are well known in the art. In another embodiment, said substrate comprises the heparin entities of the invention and a coating that comprises a compound that causes a bioactive response. Said substrate comprises the materials referred to above and below. In one embodiment, said substrate is ePTFE.

Other suitable substrates include, but are not limited to, cellulosics, agarose, alginate, polyhydroxyethylmethacrylate, polyvinyl pyrrolidone, polyvinyl alcohol, polyallylamine, polyallylalcohol, polyacrylamide, and polyacrylic acid.

Additionally, certain metals and ceramics may be used as substrates for the present invention. Suitable metals include, but are not limited to, titanium, stainless steel, gold, silver, rhodium, zinc, platinum, rubidium, and copper, for example. Suitable alloys include cobalt-chromium alloys such as L-605, MP35N, Elgiloy, nickel-chromium alloys (such as Nitinol), and niobium alloys, such as Nb-1% Zr, and others.

Suitable materials for ceramic substrates include, but are not limited to, silicone oxides, aluminum oxides, alumina, silica, hydroxyapapitites, glasses, calcium oxides, polysilanols, and phosphorous oxide. In another embodiment, protein-based substrates, such as collagen can be used. In another embodiment, polysaccharide-based substrates, such as cellulose can be used.

Some substrates may have multiplicities of reactive chemical groups populating at least a portion of its surface to which heparin entities of the invention can be bound. Said heparin entities of the invention are covalently bound to the substrate material through said reactive chemical groups. Surfaces of said substrates can be smooth, rough, porous, curved, planar, angular, irregular, or combinations thereof. In some embodiments, substrates with surface pores have internal void spaces extending from the porous surface of the material into the body of the material. These porous substrates have internal substrate material bounding the pores that often provides surfaces amenable to immobilizing biologically active entities. Whether porous or non-porous, substrates can be in the form of filaments, films, sheets, tubes, meshworks, wovens, non-wovens, and combinations thereof.

Substrates lacking reactive chemical groups on their surfaces (or lacking appropriately reactive chemical groups) can be covered, at least in part, with a polymeric covering material having a multiplicity of reactive chemical groups thereon to which said heparin entities can be bound. Polymeric substrates can also be modified along their surface, or along their polymer backbone using a variety of methods, including hydrolysis, aminolysis, photolysis, etching, plasma modification, plasma polymerization, carbene insertion, nitrene insertion, etc. Said heparin entities are covalently attached, or bound, to the polymeric covering material through the reactive chemical groups of the covering material or directly to a substrate that has been modified. The polymeric covering material may form at least one layer on at least a portion of a substrate.

There are many other surface modifications, such those described U.S. Pat. No. 4,600,652 and U.S. Pat. No. 6,642,242, which are based on substrates having a layer of a polyurethane urea to which heparin modified to contain aldehyde groups through oxidation with nitrous acid or periodate, may be bound by covalent links. A similar technology is described in U.S. Pat. No. 5,032,666, where the substrate surface is coated with an amine rich fluorinated polyurethane urea before immobilization of an antithrombogenic agent, such as an aldehyde-activated heparin. Another antithrombogenic surface modification which may be mentioned is described in publication WO87/07156. The surface of the device is modified through the coating with a layer of lysozyme or a derivative thereof to which heparin is adhered. Yet another surface modification for producing antithrombogenic articles is described in U.S. Pat. No. 4,326,532. In this case, the layered antithrombogenic surface comprises a polymeric substrate, a chitosan bonded to the polymeric substrate and an antithrombogenic agent bonded to the chitosan coating. Others have reported an antithrombogenic hemofilter also using a chitosan layer for binding heparin. Another process for preparing antithrombogenic surfaces is described in WO97/07834, wherein the heparin is admixed with sufficient periodate so as not to react with more than two sugar units per heparin molecule. This mixture is added to a surface modified substrate of a medical device, wherein said surface modification contains amino groups. The above listing of processes for adding reactive groups to substrates are only a small example of how this can be accomplished. The above listing is by no means complete. Furthermore, it is clear that the type of process used to add reactive chemical groups to a substrate will depend on the properties of the substrate of which a person of skill in the art will recognize.

In another embodiment of the invention, said medical substrate comprising said bound heparin entity via at least one heparin molecule is a component of a medical device. Medical devices comprise, but are not limited to, grafts, vascular grafts, stents, stent-grafts, bifurcated grafts, bifurcated stents, bifurcated stent-grafts, hernia patches, hernia plugs, periodontal grafts, surgical fabrics, drug delivery devices, catheters, cardiac leads balloons and indwelling filters. In one embodiment, said stents can be used in cardiac, peripheral or neurological applications. In another embodiment, said stent-grafts can be used in cardiac, peripheral or neurological applications.

Another embodiment of the invention comprises a heparin entity comprising at least one heparin molecule and at least one core molecule. As shown in FIG. 1, the core molecule 102 is the "backbone" of the heparin entity 100 to which heparin molecules 104 are bound. Said core molecule 102 can be either cyclic (102a, FIGS. 1A and 1C), linear (102b, FIG. 1B), branched, dendritic, "Y" shaped, "T" shaped, or "star" shaped as described by Freudenberg, U., Biomaterials, 30, 5049-5060, 2009 and Yamaguchi, N., Biomacromolecules, 6, 1921-1930, 2005. In one embodiment, said core molecule is selected from the group consisting of proteins (including polypeptides), hydrocarbons, lipids, aminoglycosides, polysaccharides and polymers. Proteins include, but are not limited to, antibodies, enzymes, receptors, growth factors, hormones, serpins and any globular protein. Specific proteins and polypeptides include, but are not limited to, albumin, colistin, collagen, polylysine, antithrombin III, fibrin, fibrinogen, thrombin, laminin, keratin, and the like. In another embodiment, said core molecule can be a polypeptide. Said polypeptide need not be very long and can comprise one or more repetitions of amino acids, for example repetitions of serine, glycine (e.g. Ser-Gly-Gly-Ser-Gly), lysine or ornithine residues. Alternatively, other amino acid sequences can be used, for example colistin, polylysine, and polymyxin.

Examples of polysaccharides include, but are not limited to neutral polysaccharides such as cellulose, starch, agarose, carboxymethylcellulose, nitrocellulose, and dextran, anionic polysaccharides such as alginate, heparin, heparin sulfate, dextran sulfate, xanthan, hyaluronic acid, carrageenan, gum arabic, tragacanth, arabinogalactan, and pectin; macrocyclic polysaccharides such as cyclodextrin and hydroxypropyl cyclodextrin; and polycationic polysaccharides such as chitin and chitosan.

Examples of synthetic polymers include, but are not limited to, polyethylene glycol (PEG) 200, 300, 400, 600, 1000, 1450, 3350, 4000, 6000, 8000 and 20000, polytetrafluoroethylene, polypropylene glycol, poly(ethylene glycol-co-propylene glycol), copolymers of polyethylene glycol, copolymers of polypropylene glycol, copolymers of tetrafluoroethylene with vinyl acetate and vinyl alcohol, copolymers of ethylene with vinyl acetate & vinyl alcohol, polyvinyl alcohol, polyethyleneimine, polyacrylic acid; polyols such as polyvinyl alcohol and polyallyl alcohol; polyanions such as acrylic acid and poly(methacrylic acid). Polycation polymers include poly(allylamine), poly(ethyleneimine), poly(guanidine), poly(vinyl amine), polyethylene glycol diamine, ethylene diamine, and poly(quaternary amines); polyacrylonitriles such as hydrolyzed polyacrylonitrile, poly(acrylamide-co-acrylonitrile), and their copolymers. Other polymers include fluorinated copolymers including copolymers of tetrafluoroethylene and vinyl alcohol, vinyl acetate, vinyl formamide, acrylamide, and vinyl amine. In another embodiment, said core molecule can be an aminoglycoside, including, but not limited to, amikacin, arbekacin, gentamicin, kanamycin, neomycin, netilmicin, paromomycin, rhodostreptomycin, streptomycin, tobramycin, and apramycin.

Heparin is a mucopolysaccharide, isolated from pig intestine or bovine lung and is heterogeneous with respect to molecular size and chemical structure. Heparin is built up from alternating glycuronic acid and glucosamine units. The glycuronic acid units consist of D-glycuronic acid and L-iduronic acid. These are respectively D- and L-(1,4)-bound to the D-glucosamine units. A large proportion of the L-iduronic acid residues are sulfated in the 2-position. The D-glucosamine units are N-sulfated, sulfated in the 6-position and are α-(1,4)-bound to the uronic acid residues. Certain D-glucosamine units are also sulfated in the 3-position. Heparin contains material with a molecular weight ranging from about 6,000 Daltons to about 30,000 Daltons. The hydroxyl and amine groups are derivatized to varying degrees by sulfation and acetylation. The active sequence in heparin responsible for its anticoagulation properties is a unique pentasaccharide sequence that binds to the ligand anti-thrombin III (ATIII). The sequence consists of three D-glucosamine and two uronic acid residues. Heparin molecules can also be classified on the basis of their pentasaccharide content. About one third of heparin contains chains with one copy of the unique pentasaccharide sequence (see, Choay, Seminars in Thrombosis and Hemostasis 11:81-85 (1985) which is incorporated herein by reference) with high affinity for ATIII, whereas a much smaller proportion (estimated at about 1% of total heparin) consists of chains which contain more than one copy of the high affinity pentasaccharide (see, Rosenberg et al., Biochem. Biophys. Res. Comm. 86:1319-1324 (1979) which is incorporated herein by reference). The remainder (approx. 66%) of the heparin does not contain the pentasaccharide sequence. Thus, so called "standard heparin" constitutes a mixture of the three species: "high affinity" heparin is enriched for species containing at least one copy of the pentasaccharide and "very high affinity" heparin refers to the approximately 1% of molecules that contain more than one copy of the pentasaccharide sequence. These three species can be separated from each other using routine chromatographic methods, such as chromatography over an anti-thrombin affinity column (e.g., Sepharose-AT; see, e.g., Lam et al., Biochem. Biophys. Res. Comm. 69:570-577 (1976) and Horner Biochem. J. 262:953-958 (1989) which are incorporated herein by reference).

In one embodiment, said heparin is derived from an animal. In another embodiment, said heparin is bovine or porcine derived. In another embodiment, said heparin is a synthetic heparin, i.e. not derived from animal sources (e.g. fondaparinux or enoxaparin). In another embodiment, heparin entities of the invention comprise heparin that has been enriched and comprises substantially pure "high affinity" heparin. In another embodiment, heparin entities of the invention comprise heparin that has been enriched and comprises substantially pure "very high affinity" heparin. In another embodiment, heparin entities of the invention comprises heparin has been enriched and comprises a combination of substantially pure "high affinity" and "very high affinity" heparin.

Another embodiment of the invention comprises the binding of said heparin entity to a medical substrate via at least one heparin molecule. As shown in FIG. 1, the heparin entities of the invention are bound to said substrate via at least one heparin molecule. Thus, in one embodiment, said bound heparin molecule is attached to said substrate via end point attachment (as depicted in FIGS. 1A and 1B). In another embodiment, said bound heparin molecule is attached to said substrate via an end point aldehyde. This can be accomplished essentially as described in U.S. Pat. No. 4,613,665, which is incorporated herein by reference in its entirety, and as described below.

In another embodiment, said heparin entity is bound onto a substrate via at least one heparin molecule, wherein said bound heparin molecule is attached to said substrate via a "loop attachment." Loop attachment, as depicted in FIG. 1C, is an attachment of said heparin entity via at least one heparin, wherein the heparin is attached loosely to the substrate in a small number of locations, therefore allowing substantial portions of the bound heparin to be exposed to heparinase (as opposed to more common methods that attach heparin tightly in a large number of locations). The more common methods of coupling heparin to a substrate comprise reacting a majority of functional groups randomly localized along a heparin molecule's length (e.g. using coupling agents such as carbodiimides, epoxides, and polyaldehydes). These methods result in a high probability that the active sequence (said unique pentasaccharide sequence describe above) will be bound to the substrate resulting in reduced and/or lost activity. In loop attachment of heparin, only a few functional groups on the heparin react and are bound to the substrate. Thus, there is a high probability that the active sequence of the attached heparin will not be bound to the substrate, therefore allowing said active sequence to bind to its ligand. In another embodiment, the invention comprises a heparin entity with multiple attachments to a substrate, wherein the active sequence is not bound to the substrate. In another embodiment, said bound heparin entity molecule is attached to said substrate via loop attachment.

As discussed above, endpoint and loop attachments allow a substantial portion of at least one heparin molecule (in a heparin entity) not to be bound to a substrate. As used herein the term "substantial portion" means that about 50%, about 60%, about 70%, about 80%, about 90%, about 95%, about 96% about 97%, about 98% and about 99% of the heparin molecule is not bound to the substrate. In another embodiment, the term also refers to the at least one heparin molecule (in a heparin entity) wherein said the at least one heparin molecule bound to the substrate is not bound to a substrate via its active sequence. Thus, since the active sequence is not bound to the surface of the substrate, the active sequence has a greater probability of interacting with its ligand. In other words, if the active sequence is bound to the surface of the substrate then there is a small chance of heparin binding to its ligand.

However, because said heparin entities are attached via heparin by endpoint and/or loop attachment, the heparin is sensitive to heparinase. Thus, after heparinase treatment, there will be very little, if any, heparin, or fragments thereof, on the surface of said substrate. In contrast, some of the more common methods of attaching heparin to the surface of a substrate (which comprises multiple bonds along the length of the heparin molecule, as described above), after heparinase treatment, will have a significant amount of heparin, or fragments thereof, still attached to the surface of the substrate. Thus, after heparinase treatment, heparin, or fragments thereof, can be detected on the surface of said substrate. Without being bound to any particular theory, the inventors have that discovered that the more sensitive the bound heparin or heparin entity is to heparinase, the more biological activity said bound heparin or heparin entity exhibits. This may be because the active sequence of the bound heparin or heparin entity is not attached to the surface of the substrate, thus said bound heparin or heparin entity has a greater chance of binding to its ligand.

Heparin must have intact conformation and structure to be recognized by ATIII, and if said conformation and structure is lost, heparin will exhibit poor activity. In addition, loss of said conformation and structure results in poor recognition by other proteins, such as heparinase-1, resulting in said heparin being resistant to depolymerization. For example, modification of soluble heparin with carbodiimide changes the soluble heparin structure in such a way that it is no longer recognized by heparinase-1, and the modified soluble heparin has reduced whole blood anticoagulant activity (see Olivera, G. B., Biomaterials, 24, 4777-4783, 2003). The inventors have discovered that heparinase sensitivity of attached heparin or heparin entity is predictive of ATIII binding activity of said attached heparin or heparin entity. Without wanting to be constrained by any particular theory, if the attached heparin or heparin entity retains specificity for specific enzymes such as heparinase-1, then the attached heparin or heparin entity retains substantially enough primary/secondary/tertiary structure for it also to have specificity for ATIII. Thus, the inventors have discovered that when an attached heparin or heparin entity is recognized by heparinase-1, said attached heparin or heparin entity is also recognized by ATIII, as exemplified by high binding activities.

The inventors have also shown that a boric acid rinse will restore heparinase sensitivity to inactivated attached heparin or heparin entities (inactivated by sterilization, mechanical compaction and expansion, or long-term storage, for example). Thus, another embodiment of the invention comprises a method of restoring heparinase sensitivity to heparin or heparin entities bound onto a substrate comprising rinsing said substrate in a solution of boric acid. In one embodiment, said substrate was exposed to a sterilization cycle. In another embodiment, said substrate was exposed to mechanical treatments that reduced heparinase-1 activity.

In another embodiment of the invention, after treating a medical substrate with bound heparin entities of the invention with heparinase, heparin, or fragments thereof, will not be detected on said substrate. In another embodiment, after treating a medical substrate with bound heparin entities of the invention with heparinase, heparin, or fragments thereof, will be detected at a substantially lower level than before heparinase treatment. Significantly lower level of detection comprises very little detection after staining and/or labeling for heparin.

In another embodiment, said heparin, or fragments thereof, will not be detected visually (macroscopically) after staining or labeling. Heparin, or fragments thereof, can be detected by a label that binds directly or indirectly to heparin, or fragments thereof. In one embodiment, said label that binds to heparin, or fragments thereof, is selected from the group consisting of dyes, antibodies, and proteins. Examples of labels include, but are not limited to proteins including anti-heparin antibodies (polyclonal or monoclonal) and ATIII; metachromatic dyes including toluidine blue, azure A, alcian blue, victoria blue 4R, night blue, methylene blue; radioiodinated labels including radioiodinated toluidine blue, radioiodinated methylene blue, radioiodinated heparin antibodies, radioiodinated ATIII; tritiated labels including tritiated toluidine blue, tritiated azure A, tritiated alcian blue, tritiated victoria blue 4R, tritiated night blue, tritiated methylene blue; carbon-14 labels including 14C-toluidine blue, 14C-azure A, 14C-alcian blue, 14C-victoria blue 4R, 14C-night blue, 14C-methylene blue; fluorescent labels including rhodamine-labelled heparin antibodies, fluorescein-labelled heparin antibodies, rhodamine-labelled ATIII, fluorescein-labelled ATIII. In another embodiment, said dye is toluidine blue. In another embodiment, after heparinase treatment, an insignificant amount of toluidine blue will bind to heparin, or fragments thereof, but will not be visually detected on said substrate (essentially as depicted in FIGS. 3B and 4E). In another embodiment, after heparinase treatment, a insignificant amount of toluidine blue will bind to residual heparin, or fragments thereof, and a reading from a detector that can measure the amount of toluidine blue (or other labels described above) on a substrate (e.g. a spectrophotometer, luminometer, densitometer, liquid scintillation counter, gamma counter, or the like) will be about background levels, or be insignificantly different from background levels when compared to a substrate without heparin entities. In another embodiment, after heparinase treatment, a reading from a detector that can measure the amount of toluidine blue (or other labels described above) on a substrate will be significantly different when compared to a substrate comprising heparin entities and stained with toluidine blue (or other labels described above) without heparinase treatment.

Another embodiment of the invention comprises a heparin entity comprising at least one heparin molecule attached to a core molecule, wherein the entity is bound to a substrate via a heparin molecule, and wherein after exposure to heparinase and toluidine blue, the substrate macroscopically evidences substantially no toluidine blue on its surface (as depicted in FIG. 3 B and FIG. 4 E).

Another embodiment of the invention comprises a heparin entity which comprises at least one heparin molecule and at least one core molecule such that when said heparin entity is bound onto a substrate via a least one heparin molecule, said heparin entity is heparinase sensitive. In one embodiment, said substrate is selected from the group consisting of polyethylene, polyurethane, silicone, polyamide-containing polymers, polypropylene, polytetrafluoroethylene, expanded-polytetrafluoroethylene, biocompatible metals, ceramics, proteins, polysaccharides, and any substrate described above. In another embodiment, said substrate is expanded-polytetrafluoroethylene. In another embodiment, said substrate is a component of a medical device. In another embodiment, said medical device is selected from the group consisting of grafts, vascular grafts, stents, stent-grafts, bifurcated grafts, bifurcated stents, bifurcated stent-grafts, patches, plugs, drug delivery devices, catheters and cardiac leads. In another embodiment, said stents can be used in cardiac, peripheral or neurological applications. In another embodiment, said stent-grafts can be used in cardiac, peripheral or neurological applications. In another embodiment, said medical device can be used in orthopedic, dermal, or gynecologic applications. In another embodiment, said core molecule comprises a cyclic, linear, branched, dendritic, "Y", "T", or star molecular structure. In another embodiment, said core molecule is selected from the group consisting of proteins, polypeptides, hydrocarbons, polysaccharides, aminoglycosides, polymers, and fluoropolymers.

In another embodiment, heparin, or fragments thereof, is detected by labels that bind to heparin, or fragments thereof. In another embodiment, said label that binds to heparin, or fragments thereof, is selected from the group consisting of dyes, polyclonal antibodies, and proteins. In another embodiment, said dye is toluidine blue. In another embodiment, after heparinase treatment, an insignificant amount of toluidine blue will bind to residual heparin, or fragments thereof, and will not be visually detected on said substrate. In another embodiment, after heparinase treatment, a insignificant amount of toluidine blue will bind to residual heparin, or fragments thereof, and a reading from a detector that can measure the amount of toluidine blue (or other labels described above) on a substrate (e.g. a spectrophotometer, luminometer, densitometer, liquid scintillation counter, gamma counter, or the like) will be about background levels, or be insignificantly different from background levels when compared to a substrate without heparin entities. In another embodiment, after heparinase treatment, a reading from a detector that can measure the amount of toluidine blue (or other labels described above) on a substrate will be significantly different when compared to a substrate comprising heparin entities and stained with toluidine blue (or other labels described above) without heparinase treatment. In another embodiment, said heparin entity is bound onto a substrate via at least one heparin molecule and wherein said bound heparin molecule is attached to said substrate via end-point attachment. In another embodiment, said heparin entity is bound onto a substrate via at least one heparin molecule, wherein said bound heparin molecule is attached to said substrate via end-point aldehyde. In another embodiment, said heparin entity is bound onto a substrate via at least one heparin molecule, wherein said bound heparin molecule is attached to said substrate via loop attachment. In another embodiment, said heparin entity is bound onto a substrate via at least one heparin molecule, wherein said bound heparin molecule is attached to said substrate via aldehydes along the length said heparin.

Another embodiment of the invention comprises an ATIII binding entity comprising: a core molecule, a polysaccharide chain attached to the core molecule, and a free terminal aldehyde moiety on the polysaccharide chain. This ATIII binding entity can then be end-point attached to a substrate via a terminal aldehyde. Another embodiment of the invention comprises an ATIII binding entity comprising: a core molecule, a polysaccharide chain attached to the core molecule, and free terminal aldehyde moieties along the length of the polysaccharide chain. This ATIII binding entity can then be looped attached to a substrate via the aldehydes along the length of the polysaccharide chain. In another embodiment, said polysaccharide chain is heparin. In another embodiment, said core molecule is selected from the group consisting of a protein, a polypeptide, a hydrocarbon, an aminoglycoside, a polysaccharide, a polymer, a fluoropolymer, or any core molecule described herein. In another embodiment, heparin is bound onto the core molecule via end-point attachment. In another embodiment, the substrate is selected from the group consisting of polyethylene, polyurethane, silicone, polyamide-containing polymers, and polypropylene, polytetrafluoroethylene, expanded-polytetrafluoroethylene and biocompatible metals, or any of the substrates described herein. In another embodiment said biocompatible metal is Nitinol. In another embodiment, said substrate is expanded-polytetrafluoroethylene. In another embodiment, said substrate is a component of a medical device. In another embodiment, said medical device is selected from the group consisting of grafts, vascular grafts, stents, stent-grafts, bifurcated grafts, bifurcated stents, bifurcated stent-grafts, patches, plugs, drug delivery devices, catheters and cardiac leads. In another embodiment, said medical device can be used in cardiac, peripheral, neurologic, orthopedic, gynecologic, or dermal applications.

Another embodiment of the invention comprises an implantable medical device comprising a medical substrate, wherein said medical substrate comprises a heparin entity bound onto a substrate via at least one heparin molecule, wherein said bound heparin entities are heparinase sensitive. In one embodiment, said medical device is selected from the group consisting of grafts, vascular grafts, stents, stent-grafts, bifurcated grafts, bifurcated stents, bifurcated stent-grafts, patches, plugs, drug delivery devices, catheters and cardiac leads. In another embodiment, said stent can be used in cardiac, peripheral or neurological applications. In another embodiment, said stent can be a balloon expandable and/or a self expanded stent. Said stents can be made from any biocompatible material including any polymer or metal as described above. In another embodiment, said stent is made from Nitinol and/or stainless steel. In another embodiment, said stent comprises a graft. In another embodiment, said graft and/or stent comprise heparin entities of the invention.

The heparin entities of the invention retain significant biological activity following immobilization and sterilization as compared to other coated medical substrates. Thus, in one embodiment said medical substrate comprises, a heparin entity bound onto a substrate via at least one heparin molecule, wherein said bound heparin entity is heparinase sensitive has an ATIII activity of about 300 pmol/cm$^2$. In another embodiment, the ATIII activity is about 250 pmol/cm$^2$, about 200 pmol/cm$^2$, about 150 pmol/cm$^2$, about 100 pmol/cm$^2$, about 50 pmol/cm$^2$, about 40 pmol/cm$^2$, about 30 pmol/cm$^2$, about 20 pmol/cm$^2$, about 10 pmol/cm$^2$ or about 5 pmol/cm$^2$. In another embodiment, after a first round of sterilization the ATIII activity of said medical substrate is about 250 pmol/cm$^2$, about 200 pmol/cm$^2$, about 150 pmol/cm$^2$, about 100 pmol/cm$^2$, about 50 pmol/cm$^2$, about 40 pmol/cm$^2$, about 30 pmol/cm$^2$, about 20 pmol/cm$^2$, about 10 pmol/cm$^2$ or about 5 pmol/cm$^2$. In another embodiment, after a second round of sterilization, the ATIII activity of said medical substrate is about 100 pmol/cm$^2$, about 90 pmol/cm$^2$, about 80 pmol/cm$^2$, about 70 pmol/cm$^2$, about 60 pmol/cm$^2$, about 50 pmol/cm$^2$, about 40 pmol/cm$^2$, about 30 pmol/cm$^2$, about 20 pmol/cm$^2$, about 10 pmol/cm$^2$ or about 5 pmol/cm$^2$. In another embodiment, after a third round of sterilization, the ATIII activity of said medical substrate is above about 50 pmol/cm$^2$, or about 70 pmol/cm$^2$, about 60 pmol/cm$^2$, about 50 pmol/cm$^2$, about 40 pmol/cm$^2$, about 30 pmol/cm$^2$, about 20 pmol/cm$^2$, about 10 pmol/cm$^2$ or about 5 pmol/cm$^2$. ATIII activity assays are well known in the art and at least one is described below. In another embodiment, said heparin entities of the invention retain significant biological activity following compression and expansion of a medical device. In another embodiment, said heparin entities of the invention retain significant biological activity following storage conditions for medical devices either in a compacted and/or expanded state.

Another embodiment of the invention comprises methods of determining the structure of a heparin entity bonded to a substrate. One method of determining the structure of a heparin entity bonded to a substrate comprises the steps of: providing a substrate comprising a heparin entity, depolymerizing the heparin entity to generate a mixture of soluble heparin fragments, detecting each soluble heparin fragment in said mixture using column chromatography, determining the identity of each detected soluble heparin fragment from above, and deriving the structure of the heparin entity from the identities of the detected soluble heparin fragments. In one embodiment, said depolymerization is by heparinase-1. In another embodiment, column chromatography is strong anion exchange-high performance liquid chromatography or SAX-HPLC.

Another embodiment of the invention comprises an implantable medical device comprising a medical substrate, wherein said medical substrate comprises a heparin entity bound onto a substrate via at least one heparin molecule, wherein said bound heparin entities are heparinase sensitive. In one embodiment, said medical device is selected from the group consisting of grafts, vascular grafts, stents, stent-grafts, bifurcated grafts, bifurcated stents, bifurcated stent-grafts, patches, plugs, drug delivery devices, catheters, cardiac leads, balloons and indwelling filters. In another embodiment, said stent can be used in cardiac, peripheral or neurological applications. In another embodiment, said stent can be a balloon expandable and/or a self expanded stent. Said stents can be made from any biocompatible material including any polymer or metal as described above. In another embodiment, said stent is made from Nitinol and/or stainless steel. In another embodiment, said stent comprises a graft. In another embodiment, said graft and/or stent comprise heparin entities of the invention.

Another embodiment of the invention comprises methods of determining the spatial distribution of a heparin entity bonded to a substrate. One method of determining the spatial distribution of a heparin entity bonded to a substrate comprises the steps of: providing a substrate comprising a heparin entity, depolymerizing the heparin entity to generate a surface comprising surface-bonded unsaturated heparin fragments, reacting the surface with a labeling reagent which introduces a detectable component to said surface-bonded unsaturated heparin fragments, detecting said surface-bonded unsaturated heparin fragment via said detectable component, and deriving the spatial distribution of the heparin entity from the presence of the surface-bonded unsaturated heparin fragments. In one embodiment, depolymerization is by heparinase-1. In another embodiment, said labeling reagent is a lanthanoid Michael-like addition organo-complex. In another embodiment, said labeling reagent is terbium tris(4-methylthio)benzoate. In another embodiment, said organo-complex comprises chemisorbed gold nanoparticles. In another embodiment, said detecting is by epifluoroscent microscopy or transmission electron microscopy.

Another embodiment of the invention comprises a system for determining the structure of a heparin entity bonded to a substrate, comprising a depolymerization solution, a labeling reagent solution, and a detector. A system is an assembly of reagents and instruments used to detect the structure and type of binding of heparin entities to a substrate. In one embodiment, said depolymerization solution comprises heparinase-1. In another embodiment, said labeling reagent solution comprises toluidine blue, and terbium tris(4-methylthio)benzoate. In another embodiment, said detector comprises SAX-HPLC, an epifluoroscent microscope, and an absorption spectroscope. In another embodiment, said assembly of reagents can be a kit.

After enzymatic heparinase-1 depolymerization of heparin and/or heparin entities that are end-point attached, heparin fragments are left are on the surface that are unsaturated, i.e. they comprise a carbon-carbon double bond ("nubs"). Enzymatic heparinase depolymerization involves cleavage of the non-reducing terminal uronic acid residue to a 4,5-unsaturated derivative. This produces residual surface-bonded unsaturated heparin fragments bonded to the substrate that comprises a carbon-carbon double bond. Thus, the structure of the residual surface-bonded heparin fragment is unsaturated, and can react with various detection molecules, including those that comprise Michael-like addition complexes, such as thiol-containing compounds and thiol-containing fluorescent compounds, such as terbium tris(4-methylthio)benzoate. Thus, in another embodiment of the invention, after enzymatic heparinase-1 depolymerization of an end-point attached heparin entity, said residual surface-bonded unsaturated heparin fragments bonded to the substrate comprising a carbon-carbon double bond are detected. This method can determine if heparin and/or heparin entities were end-point attached to a substrate. In another embodiment, nub detection is combined with any of the detection and/or characterization methods described above.

This invention is further illustrated by the following Examples which should not be construed as limiting. The contents of all Figures and references are incorporated herein by reference.

EXAMPLES

Example 1

This example describes the construction of heparin entities comprising heparin and colistin sulfate as the core. This heparin entity contains free terminal aldehydes that can be used for attachment to a surface of a substrate.

Colistin sulfate (0.10 g, Alpharma, Inc.) was dissolved in 300 ml of deionized (DI) water containing MES buffer (pH 4.7, BupH™ Thermo Scientific). To this was added 10 g USP heparin, 4 g N-hydroxysulfosuccinimide (sulfo-NHS, Thermo Scientific), and 4 g of 1-ethyl-3-(3-dimethylaminopropyl)carbodiimide (EDC hydrochloride, Sigma-Aldrich, St. Louis, Mo.). The reaction was allowed to proceed at room temperature for 4 hours, followed by dialysis overnight with a 50,000 MWCO membrane (Spectra/Por®). The retentate (about 350 ml out of 500 ml) was transferred to a beaker, and cooled to 0° C. Sodium nitrite (10 mg) and acetic acid (2 ml) were added and the reaction was allowed to proceed for 1 hour at 0° C. Dialysis was performed overnight with a 50,000 MWCO membrane with the addition of 1 g NaCl to the dialysis liquid. Freezing and lyophilization of the retentate produced a fine powder.

Example 2

This example describes the construction of heparin entities comprising heparin and neomycin sulfate as the core. This heparin entity contains free terminal aldehydes that can be used for attachment to a surface of a substrate.

Neomycin sulfate (0.0646 g, Spectrum Chemical) was dissolved in 300 ml of DI water containing MES buffer (pH 4.7, BupH™ Thermo Scientific). To this was added 10 g USP heparin, 4 g N-hydroxysulfosuccinimide (sulfo-NHS), and 4 g of EDC hydrochloride. The reaction was allowed to proceed at room temperature for 4 hours, followed by dialysis overnight with a 50,000 MWCO membrane (Spectra/Por®). The retentate (about 400 ml out of 505 ml) was transferred to a beaker and cooled to 0° C. Sodium nitrite (10 mg) and acetic acid (2 ml) were added and the reaction was allowed to proceed for 1 hour at 0° C. Dialysis was performed overnight with a 50,000 MWCO membrane with the addition of 1 g NaCl to the dialysis liquid. The dialyzed retentate was filtered twice using a 20 micrometer, 0.00079 inches U.S.A. standard testing sieve, A.S.T.M.E.-11 specification NO. 635 to remove small particles. Freezing of the filtrate and lyophilization produced a fine powder.

Example 3

This example describes the construction of heparin entities comprising heparin and capreomycin sulfate as the core. This heparin entity contains free terminal aldehydes that can be used for attachment to a surface of a substrate.

Capreomycin sulfate (0.0501 g, Sigma-Aldrich, St. Louis, Mo.) was dissolved in 300 ml of DI water containing MES buffer (pH 4.7, BupH™ Thermo Scientific). To this was added 10 g USP heparin, 4 g N-hydroxysulfosuccinimide (sulfo-NHS), and 4 g of EDC hydrochloride. The reaction was allowed to proceed at room temperature for 4 hours. The reaction mixture was filtered once using a 20 micrometer, 0.00079 inches U.S.A. standard testing sieve, A.S.T.M.E.-11 specification NO. 635 to remove small particles and the filtrate was dialyzed overnight with a 50,000 MWCO membrane (Spectra/Por®). The retentate (about 400 ml out of 515 ml) was transferred to a beaker and cooled to 0° C. Sodium nitrite (10 mg) and acetic acid (2 ml) were added and the reaction was allowed to proceed for 1 hour at 0° C. Dialysis was performed overnight with a 50,000 MWCO membrane with the addition of 1 g NaCl to the dialysis liquid. The retentate was filtered twice using a 20 micrometer, 0.00079 inches U.S.A. standard testing sieve, A.S.T.M.E.-11 specification NO. 635 to remove small particles. Freezing of the filtrate and lyophilization produced a fine powder.

Example 4

This example describes the construction of heparin entities comprising heparin and poly-L-lysine as the core. This heparin entity contains free terminal aldehydes that can be used for attachment to a surface of a substrate.

Poly-L-lysine (0.1776 g, Sigma-Aldrich, molecular weight 1,000 to 5,000 g/mole) was dissolved in 300 ml of DI water containing MES buffer (pH 4.7, BupH™ Thermo Scientific). To this was added 10 g USP heparin, 4 g N-hydroxysulfosuccinimide (sulfo-NHS), and 4 g of EDC hydrochloride. The reaction was allowed to proceed at room temperature for 4 hours followed by dialysis overnight with a 50,000 MWCO membrane (Spectra/Por®). The retentate (about 400 ml out of 505 ml) was transferred to a beaker and cooled to 0° C. Sodium nitrite (10 mg) and acetic acid (2 ml) were added and the reaction was allowed to proceed for 1 hour at 0° C. Dialysis was performed overnight with a 50,000 MWCO membrane with the addition of 1 g NaCl to the dialysis liquid. Freezing of the retentate and lyophilization produced a fine powder.

Example 5

This example describes the construction of heparin entities comprising heparin and polyethyleneimine (PEI) as the core. This heparin entity contains free terminal aldehydes that can be used for attachment to a surface of a substrate.

PEI (Lupasol, BASF, 1.7756 g) was dissolved in 300 ml of DI water containing MES buffer (pH 4.7, BupH™ Thermo Scientific). To this was added 10 g USP heparin, 4 g N-hydroxysulfosuccinimide (sulfo-NHS), and 4 g of EDC hydrochloride. The reaction was allowed to proceed at room temperature for 4 hours followed by dialysis overnight with a 50,000 MWCO membrane (Spectra/Por®). The retentate (about 400 ml out of 505 ml) was transferred to a beaker and cooled to 0° C. Sodium nitrite (10 mg) and acetic acid (2 ml) were added and the reaction was allowed to proceed for 1 hour at 0° C. Dialysis was performed overnight with a 50,000 MWCO membrane with the addition of 1 g NaCl to the dialysis liquid. Freezing of the retentate and lyophilization produced a fine powder.

Example 6

This example describes the construction of heparin entities comprising heparin and ethylene diamine (EDA) as the core. This heparin entity contains free terminal aldehydes that can be used for attachment to a surface of a substrate.

EDA (0.0043 g, Sigma-Aldrich, St. Louis, Mo.) was neutralized to a pH of 4.7 with equal volume dilution of HCl and DI water, with the use of an ice bath, then dissolved in 300 ml of DI water containing MES buffer (pH 4.7, BupH™ Thermo Scientific). To this was added 10 g USP heparin, 4 g N-hydroxysulfosuccinimide (sulfo-NHS), and 4 g of EDC hydrochloride. The reaction was allowed to proceed at room temperature for 4 hours followed by dialysis overnight with a 50,000 MWCO membrane (Spectra/Por®). The retentate (about 400 ml out of 505 ml) was transferred to a beaker and cooled to 0° C. Sodium nitrite (10 mg) and acetic acid (2 ml) were added and the reaction was allowed to proceed for 1 hour at 0° C. Dialysis was performed overnight with a 50,000 MWCO membrane with the addition of 1 g NaCl to the dialysis liquid. Freezing of the retentate and lyophilization produced a fine powder.

Example 7

The heparin entities containing free terminal aldehydes of Examples 1 through 6 were immobilized onto the surface of an ePTFE substrate and tested for ATIII activity.

An ePTFE substrate material in sheet form was obtained from W.L. Gore & Associates, Inc., Flagstaff, Ariz. under the trade name GORE™ Microfiltration Media (GMM-406). A covering material in the form of a base coating was applied to the ePTFE material by mounting the material on a ten centimeter (10 cm) diameter plastic embroidery hoop and immersing the supported ePTFE material first in 100% isopropyl alcohol (IPA) for about five minutes (5 min) and then in a solution of polyethylene imine (PEI, Lupasol, BASF) and IPA in a one to one ratio (1:1). LUPASOL® water-free PEI was obtained from BASF and diluted to a concentration of about four percent (4%) and adjusted to pH 9.6. Following immersion of the ePTFE material in the solution for about fifteen minutes (15 min), the material was removed from the solution and rinsed in DI water at pH 9.6 for 15 min. PEI remaining on the ePTFE material was cross-linked with a 0.05% aqueous solution of glutaraldehyde (Amresco) at pH 9.6 for 15 min. Additional PEI was added to the construction by placing the construction in a 0.5% aqueous solution of PEI at pH 9.6 for 15 min and rinsing again in DI water at pH 9.6 for 15 min. The imine formed as a result of the reaction between glutaraldehyde and the PEI layer is reduced with a sodium cyanborohydride ($NaCNBH_3$) solution (5 g dissolved in 1 L DI water, pH 9.6) for 15 min and rinsed in DI water for thirty minutes (30 min).

An additional layer of PEI was added to the construction by immersing the construction in 0.05% aqueous glutaraldehyde solution at pH 9.6 for 15 min, followed by immersion in a 0.5% aqueous solution of PEI at pH 9.6 for 15 min. The construction was then rinsed in DI water at pH 9.6 for 15 min. The resultant imines were reduced by immersing the construction in a solution of $NaCNBH_3$ (5 g dissolved in 1 L DI water, pH 9.6) for 15 min followed by a rinse in DI water for 30 min. A third layer was applied to the construction by repeating these steps. The result was a porous hydrophobic fluoropolymeric base material, or disk having a hydrophilic cross-linked polymer base coat on substantially all of the exposed and interstitial surfaces of the base material.

An intermediate chemical layer was attached to the polymer base coat in preparation for placement of another layer of PEI on the construction. The intermediate ionic charge layer was made by incubating the construction in a solution of dextran sulfate (Amersham Pharmacia Biotech) and sodium chloride (0.15 g dextran sulfate and 100 g NaCl dissolved in 1 L DI water, pH 3) at 60° C. for ninety minutes (90 min) followed by rinsing in DI water for 15 min.

A layer of PEI, referred to herein as a "capping layer" was attached to the intermediate layer by placing the construction in a 0.3% aqueous solution of PEI (pH 9) for about forty-five minutes (45 min) followed by a rinse in a sodium chloride solution (50 g NaCl dissolved in 1 L DI water) for twenty minutes (20 min). A final DI water rinse was conducted for 20 min.

The heparin entities containing free terminal aldehydes of Examples 1 through 6 were attached, or conjugated, to the PEI layer(s) by placing the construction in a heparin entity-containing sodium chloride salt solution (approximately 0.9 g of heparin entity containing free terminal aldehydes, 5.88 g NaCl dissolved in 200 ml DI water, pH 3.9) and kept for ten minutes (10 min) at 60° C. A 572 µL volume of a 2.5% (w/v) aqueous $NaCNBH_3$ solution was added to the (200 ml) heparin entity solution. Samples were kept for additional one hundred ten minutes (110 min) at the above temperature.

The samples were then rinsed in DI water for 15 min, borate buffer solution (10.6 g boric acid, 2.7 g NaOH and 0.7 g NaCl dissolved in 1 L DI water, pH 9.0) for 20 min, and finally in DI water for 15 min followed by lyophilization of the entire construction to produce a dry construct comprising a heparin entity bound to the surface of the ePTFE substrate material. The presence and uniformity of the macromolecular construct of heparin was determined by staining samples of the construction on both sides with toluidine blue. The staining produced an evenly stained surface indicating heparin was present and uniformly bound to the ePTFE material.

Samples approximately one square centimeter (1 cm$^2$) in nominal size were cut from the construction and assayed for heparin activity by measuring the ATIII binding capacity of the heparin entities containing free terminal aldehydes that were end-point attached onto the surface of the ePTFE substrate. The assay is described by Larsen M. L., et al., in "Assay of plasma heparin using thrombin and the chromogenic substrate H-D-Phe-Pip-Arg-pNA (S-2238)." Thromb Res 13:285-288 (1978) and Pasche B., et al., in "A binding of antithrombin to immobilized heparin under varying flow conditions." Artif. Organs 15:281-491 (1991), both of which are incorporated by reference herein for all purposes. The results were expressed as amount of ATIII bound per unit surface area substrate material in picomoles per square centimeter (pmol/cm$^2$). All samples were maintained in a wet condition throughout the assay. It is important to note that while the approximately one square centimeter (1 cm$^2$) samples each have a total surface area of two square centimeters (2 cm$^2$) if both sides of the material are considered, only one surface on the sample (i.e., 1 cm$^2$) was used for calculating ATIII heparin entity-binding activity in pmol/cm$^2$.

Lyophilized samples representing each conjugated constructs produced in Examples 1 through 6 were placed in an individual Tower DUALPEEL® Self Sealing Pouch (Allegiance Healthcare Corp., McGraw Park, Ill.) and sealed for EtO sterilization. Ethylene oxide sterilization was carried out under conditions of conditioning for one hour (1 hr), an EtO gas dwell time of 1 hr, a set point temperature of 55° C., and an aeration time of twelve hours (12 hrs). Sterilization with EtO was repeated up to 3 times with samples taken after each EtO sterilization.

Figure 2:
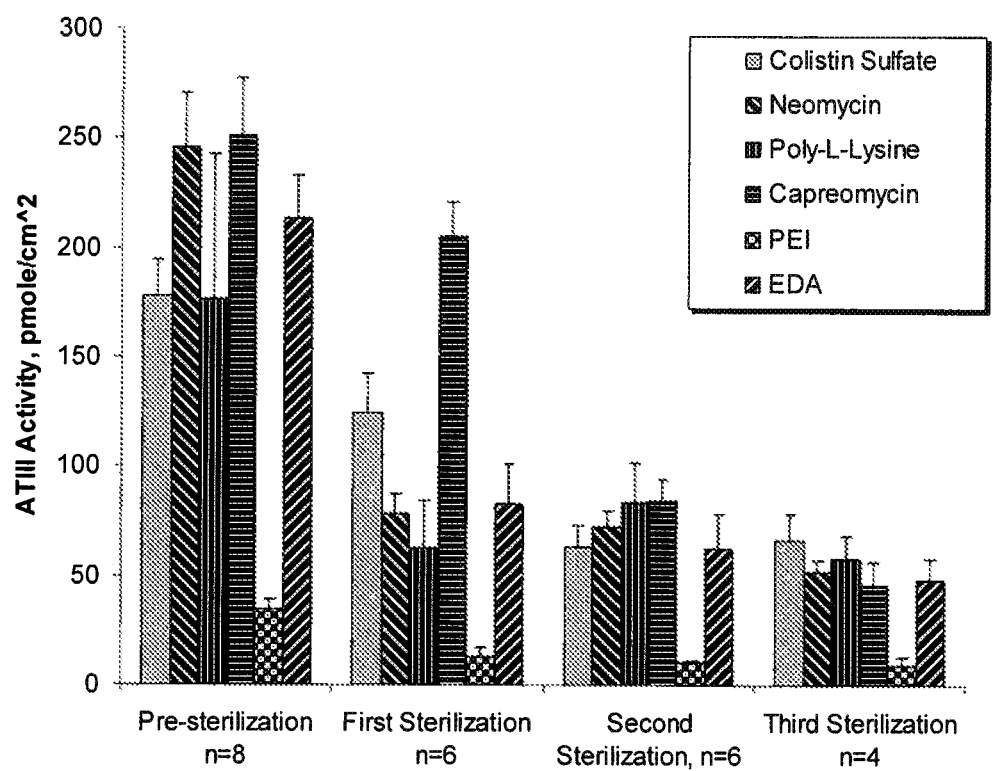
FIG. 2 depicts ATIII binding capacity of various aldehyde containing heparin entities conjugated onto expanded polytetrafluoroethylene (ePTFE) and having undergone multiple EtO sterilizations. Aldehyde containing heparin entities are classified according to the core molecule used in the synthesis of the heparin entity. Hence, colistin sulfate as the core refers to Examples 1, neomycin to Example 2, poly-L-lysine to Example 4, capreomycin to Example 3, polyethyleneimine (PEI) to Example 5, and ethylene diamine (EDA) to Example 6. All bars represent mean values of samples numbers with error bars for the standard deviation.

FIG. 2 is a bar graph illustrating the ATIII binding capacity of heparin entities containing free terminal aldehydes from Examples 1 through 6 immobilized onto an ePTFE surface and having undergone up to three EtO sterilization cycles. Anti-thrombin III binding activity is expressed as picomoles of bound anti-thrombin III per square centimeter of substrate material. As seen from the results, all conjugated heparin entities containing free terminal aldehydes resulted in high anti-thrombin III binding activity before sterilization and following up to three EtO sterilizations. All bars represent mean values of sample numbers with error bars for the standard deviation.

Example 8

The heparin entities containing free terminal aldehydes produced in Examples 2, 3, 4, and 6 were analyzed in order to determine their absolute molecular weights.

A Waters 2414 RI detector in conjunction with Wyatt ASTRA 5.3.4.10 software was used to determine the dn/dc for USP heparin in 100 mM NaNO$_3$ with 0.02% NaN$_3$ at a laser wavelength of 660 nm. The dn/dc (change in refractive index divided by change in concentration) for USP heparin was determined by plotting known concentrations of heparin versus the RI detector response and calculating the slope.

The heparin entities were analyzed with a Wyatt-Dawn Helleos-II 18-angle light scattering detector (Wyatt Technology Corp.) for measurement of absolute molecular weight, with detectors 1, 2, 3, 4, 17, and 18 not utilized. A stock solution of the heparin entity was prepared in 100 mM NaNO$_3$ with 0.02% NaN$_3$ mobile phase. From this stock solution the following concentrations were made: 0.5 mg/mL, 1.0 mg/mL, 1.5 mg/mL, 2.0 mg/mL, and 2.5 mg/mL for the heparin entities of Examples 3 and 4. For the heparin entities of Examples 2 and 6, concentrations of 0.25 mg/mL, 0.5 mg/mL, 1.0 mg/mL, 1.5 mg/mL, and 2.0 mg/mL were made. Each sample was filtered with a 0.02 micron syringe filter using a 5 ml syringe prior to injection into the light scattering detector. Batch data analysis was performed on all samples using a Zimm plot and the dn/dc for USP heparin (0.126 Ug). Table 1 depicts the absolute molecular weights.

TABLE 1

Absolute Molecular Weight Values for Heparin Entities

| Example # | Core Molecule | Mw (g/mol) |
|---|---|---|
| 2 | Neomycin | 18,570 |
| 3 | Capreomycin | 17,710 |
| 4 | Poly-L-Lysine | 20,300 |
| 6 | EDA | 21,850 |
|   | USP Heparin | 14,810 |

All heparin entities analyzed for absolute molecular weight showed values larger than USP heparin (14,810 g/mol), with the values ranging from 17,710 g/mol for the heparin entity comprising heparin and capreomycin as the core, to 21,850 g/mol for the heparin entity comprising heparin and EDA as the core.

Example 9

This example demonstrates a detection method for discerning the method of attachment of heparin or a heparin entity onto a surface of a substrate. Specifically, this example looks at attachment of heparin and heparin entities via immobilization onto an ePTFE substrate, using a single point attachment comprising free-terminal aldehydes, and using a multi-point attachment comprising carbodiimide conjugation.

Heparin end-point aldehyde was made according to U.S. Pat. No. 4,613,665 and immobilized onto PEI-ePTFE substrates as described in Example 7. This produced a surface in which the heparin was immobilized by end-point attachment. Heparin attachment was demonstrated by staining a sample with toluidine blue and noting the coloration, as shown in FIG. 3 A.

A surface was also produced in which the heparin end-point aldehyde was attached not by the free terminal aldehyde, but by multiple carboxylic acid residues along the heparin chain length using 1-ethyl-3-(3-dimethylaminopropyl) carbodiimide (EDC). EDC conjugation of heparin onto a surface is known to bind the heparin through a multiplicity of sites. A PEI containing disk of Example 7 was immersed into 300 ml of 0.1 MES buffer (pH 4.7). To this solution, 1 gram of heparin with end-point aldehydes and 4 grams EDC hydrochloride was added. The reaction was allowed to proceed at room temperature for 4 hours. The immobilized heparin disk was rinsed with DI water, borate buffer, and a final DI water rinse.

A surface was also produced in which USP heparin containing no free terminal aldehydes was attached by EDC through multiple bond sites on the surface. A PEI containing disks of Example 7 was immersed into 300 ml of 0.1 MES buffer (pH 4.7). To the solution, 1 gram USP heparin and 4 grams EDC hydrochloride was added. The reaction was allowed to proceed at room temperature for 4 hours. The immobilized heparin disk was rinsed with DI-water, borate buffer, and a final DI water rinse.

The heparin entity of Example 2 immobilized onto ePTFE/PEI as described in Example 7 was also produced. Alternatively, the heparin entity of Example 2 was immobilized onto ePTFE/PEI using carbodiimide conjugation. A PEI containing disk of Example 7 was immersed into 300 ml of 0.1 MES buffer (pH 4.7). To the solution, 1 gram of the heparin entity of Example 2 and 4 grams EDC hydrochloride was added. The reaction was allowed to proceed at room temperature for 4 hours. The immobilized heparin entity disk was rinsed with DI water, borate buffer, and a final DI water rinse.

To demonstrate that heparin and heparin entities were immobilized by each technique described above, samples approximately 1×1 cm were stained with toluidine blue. It was noted that all samples stained with toluidine blue similar to FIG. 3 A (which depicts USP heparin end-point aldehyde immobilized by end-point attachment).

For each of the various ePTFE-PEI disks conjugated with heparin and heparin entity, a 2×2 cm square was cut and placed in a 1.5 ml vial. To this was added 1 ml of heparinase-1 (from *Flavobacterium heparinum*, E.C. 4.2.2.7, Sigma-Aldrich, St. Louis, Mo.) diluted to 1 mg/mL in the following buffer: 20 mM Tris-HCl, pH 7.5, 50 mM NaCl, 4 mM CaCl2, 0.01% BSA. The sample was incubated for 30 minute at room temperature, rinsed with DI-water, and stained with toluidine blue. Samples that where end-point attached, and not multi-point attached, appeared substantially less stained, as shown in FIG. 3 B for USP heparin end-point aldehyde immobilized by end-point attachment. Multi-point immobilized heparin entities retained stain.

Quantitation of the staining was performed utilizing luminosity measurements for each of the samples. Samples were mounted onto glass slides and secured with a single strip of adhesive tape. Digital images were taken with an Olympus SZX12 microscope (Olympus America Inc.) equipped with an Olympus DP71 digital camera controlled with DP Controller 3.1.1.267 software. Images were captured using a 1× lens at 7× magnification with exposure set to 1/350 sec and lighted with an overhead ring-light. Before capture of final images, images were examined to ensure saturation was not exceeded. It is important to note that stained samples, i.e., those that stained substantially with toluidine blue, produced low luminosity values, while those that did not stain substantially produced high luminosity values (the luminosity scale for this example ranged from 0 to 255).

The luminosity of each captured digital image was assessed using Adobe Photoshop Elements 2.0 (Adobe Systems Inc., San Jose, Calif.). Within Adobe Photoshop Elements 2.0 the image was loaded (resolution of 144 pixels/inch) and a representative rectangular region of the sample was outlined using the rectangular marquee tool. From the top tool bar, image was selected followed by selection of histogram. The histogram window opened, with the channel set to luminosity. The mean is recorded as the mean luminosity.

All samples conjugated with heparin and heparin entity (tabulated with luminosity values in Table 2) stained substantially with toluidine blue, indicating dense coverage of attached heparin and heparin entity on the substrate. Luminosity values after immobilization and staining ranged from 27.3 for heparin end-point aldehyde immobilized by end-point attachment to 139.1 for USP heparin immobilized by multi-point attachment with EDC. After heparinase-1 treatment and staining, luminosity values increased for all samples, indicating a loss of heparin and a consequential decrease in staining and in coloration. For samples more sensitive to heparinase-1, the change is more significant. This change is demonstrated in a graph of normalized change in luminosity. The term "normalized change in luminosity" is defined as the luminosity value after immobilization subtracted from the luminosity value after heparinase-1 treatment divided by the luminosity after immobilization value, with the resultant multiplied by 100, i.e., {[(luminosity(post heparinase)−luminosity(pre heparinase)]÷luminosity(pre heparinase)}*100. Normalized change in luminosity for each of the samples in Table 2 is shown in FIG. 3 C, displayed as a function of heparin entity type and immobilization attachment method. The normalized change in luminosity of heparin end-point aldehyde was dependent upon the immobilization attachment method, with end-point attachment giving a value of 603 and multi-point attachment giving a value of 66. This dependency was observed for the heparin entity of heparin and neomycin with an end-point attachment value of 231 and multi-point attachment of 16. USP heparin with multi-point attachment also exhibited a low normalized change in luminosity with a value of 14. Low values in normalized change in luminosity indicated a surface resistant to heparinase-1 and hence small quantities of heparin removed.

The heparinase-1 was effective at removing the heparin or heparin entity from the surface, as indicated by a lack of substantial staining by toluidine blue and a consequential lack of coloration, and a consequential high value for normalized change in luminosity. Heparinase-1 was utilized to discern whether heparin or a heparin entity was attached via free terminal aldehydes or via multi-point attachment using carbodiimide conjugation.

TABLE 2

Luminosity Values

| Heparin Entity | Immobilization Method | Luminosity after Immobilization & Staining | Luminosity after Heparinase-1 & Staining |
|---|---|---|---|
| Heparin end-point aldehyde | End-point | 27.3 | 192.3 |
| Heparin end-point aldehyde | EDC multi-point | 73.6 | 122.8 |
| USP heparin | EDC multi-point | 139.1 | 158.9 |
| Heparin and neomycin core Example 2 | EDC multi-point | 82.8 | 96.2 |
| Heparin and neomycin core Example 2 | End-point | 57.0 | 189.3 |

Example 10

This example demonstrates a detection method for discerning the method of attachment of a heparin entity onto a surface of a substrate after sterilization. Specifically, this example looks at attachment of heparin entities via immobilization onto an ePTFE substrate, using a single point attachment comprising free-terminal aldehydes followed by sterilization and a boric acid rinse.

The heparin entity of Example 6 was immobilized onto ePTFE as described in Example 7. Samples where shown to have good heparin coverage as indicated by toluidine blue staining (as shown in FIG. 4A). Other end-point attached samples were sterilized, as described in Example 7, via 3 cycles of EtO, as described in Example 7. A portion of these samples was rinsed in DI water for 15 min, borate buffer solution (10.6 g boric acid, 2.7 g NaOH and 0.7 g NaCl dissolved in 1 L DI water, pH 9.0) for 20 min, and finally in DI water for 15 min after sterilization and before toluidine blue staining and measuring luminosity as described in Example 9.

Samples having undergone sterilization but no boric acid rinse stained with toluidine blue before heparinase-1 treatment (FIG. 4B) and after (FIG. 4C). Both samples indicate the presence of heparin entity by coloration and low luminosity values of 31. 7 and 85.6, respectively. Sterilization has appeared to diminish the ability of heparinase-1 to depolymerize the heparin entity bound by the free terminal aldehyde, as compared to heparin entity that was not sterilized.

Samples having undergone sterilization and boric acid rinse were stained with toluidine blue before heparinase-1 treatment (FIG. 4D) and after (FIG. 4E). Dense heparin entity coverage was indicated before heparinase-1 treatment by toluidine blue stain and a luminosity value of 54.4, while the sample receiving the boric acid rinse and heparinase-1 had essentially no toluidine blue stain and a luminosity value of 186.3, indicating substantial heparinase sensitivity of attached heparin entity.

This example shows that boric acid restored heparin conformation of the attached heparin entity, exemplified by high ATIII specificity and heparinase sensitivity. Without wishing to be bound by theory, it is hypothesized sterilization altered the conformation of the immobilized heparin entity layer, substantially reducing specificity for ATIII (as evidenced by low activity) and reducing heparinase sensitivity (as evidenced by substantial staining with toluidine blue). It is further hypothesized the boric acid rinse restored conformation to the attached heparin entity layer that was altered by sterilization. Restoration of conformation resulted in sensitivity of the attached heparin entity to heparinase-1 depolymerization, as shown by lack of staining in FIG. 4E. It is further hypothesized that if an attached heparin entity has a conformation that heparinase-1 recognizes, then ATIII will recognize the attached heparin entity, and visa versa.

Example 11

This example demonstrates a detection method for determining the composition of the heparin entities using oligosaccharide mapping of heparinase-1 depolymerized heparin entities with strong anion exchange-high performance liquid chromatography (SAX-HPLC).

USP Heparin and the heparin entities of Examples 1 and 2 were dissolved at 0.1 mg in 100 µl of 50 mM acetate buffer, pH 7.3, containing 2.5 mmol of calcium acetate. The USP heparin and the heparin entities of Examples 1 and 2 were depolymerized to their constituent oligosaccharides by the addition of 6 milliunits of heparinase-1 for 15 hrs at 30° C., and flash frozen at −85° C.

Analysis of the oligosaccharides from each sample were performed by SAX-HPLC and quantified at 232 nm using a 5 micron SAX column (150×4.6 mm; Spherisorb, Waters). Isocratic separation was performed from 0 to 5 min with 50 mM NaCl, pH 4.0, and linear gradient separation was performed from 5 to 90 min with 100% 50 mM NaCl, pH 4.0, to 100% 1.2 M NaCl, pH 4.0, at a flow of 1.2 mL/min.

Figure 5A:
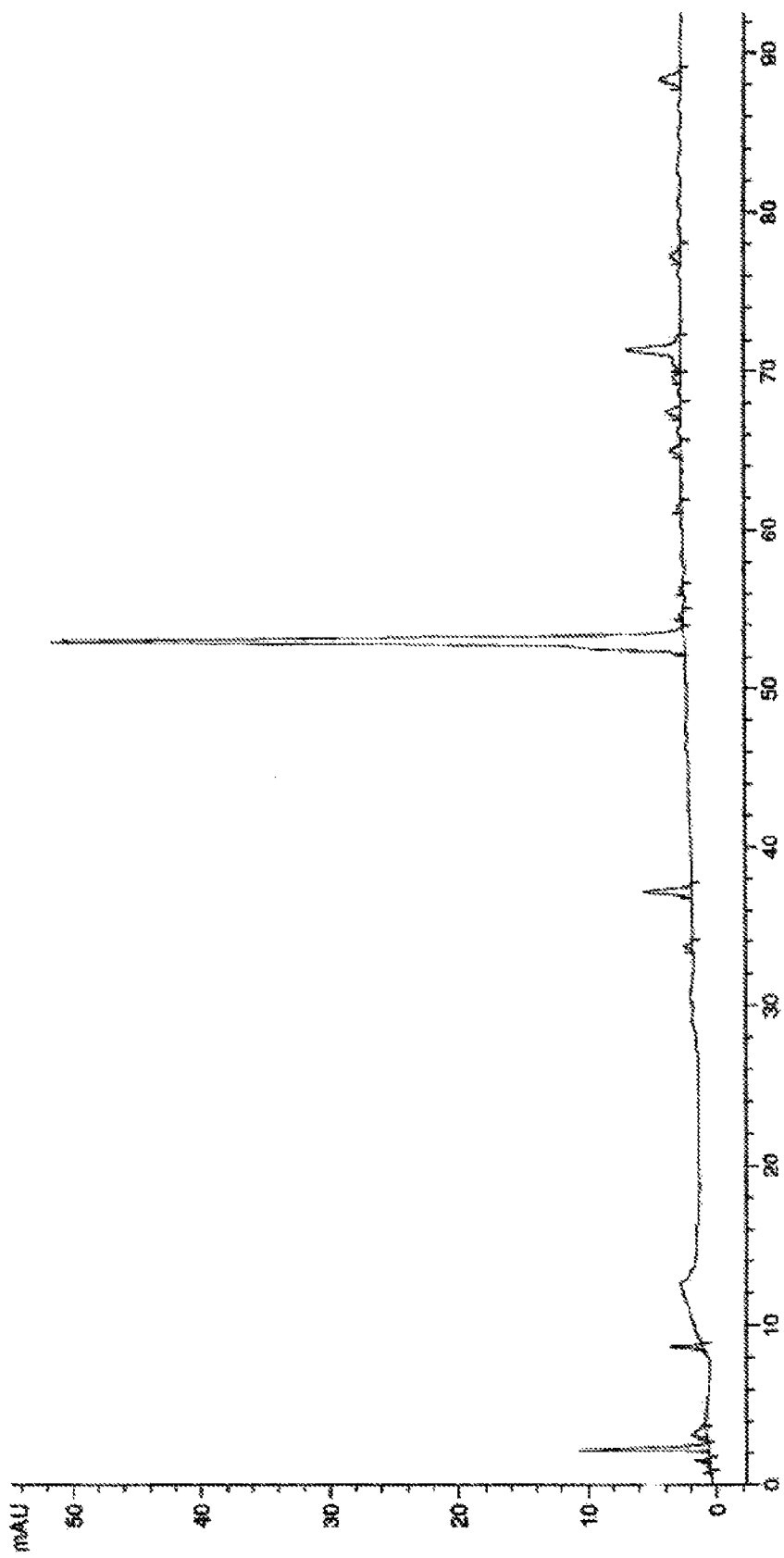
FIGS. 5 A-C depicts SAX-HPLC chromatograms from heparinase-1 depolymerization of (A) USP heparin, (B) heparin entities constructed from heparin and colistin sulfate, and (C) heparin entities constructed from heparin and neomycin sulfate.

FIG. 5 shows qualitative maps of (A) depolymerized USP heparin, (B) the depolymerized heparin entity of Example 1 comprising heparin and a core comprising colistin sulfate, and (C) the depolymerized heparin entity of Example 2 comprising heparin and a core comprising neomycin sulfate. The chromatogram for USP heparin was the base line case and served as a standard of reference for the heparin entities of Examples 1 and 2. Each peak in FIG. 5A represents a unique depolymerized oligosaccharide fragment characteristic of USP heparin. New peaks, as indicated by the vertical arrows in FIGS. 5 B and C, represent novel oligosaccharides units distinct from USP heparin, and hence, allowed the identification of heparin entities through these distinct signature peaks.

Figure 5B:
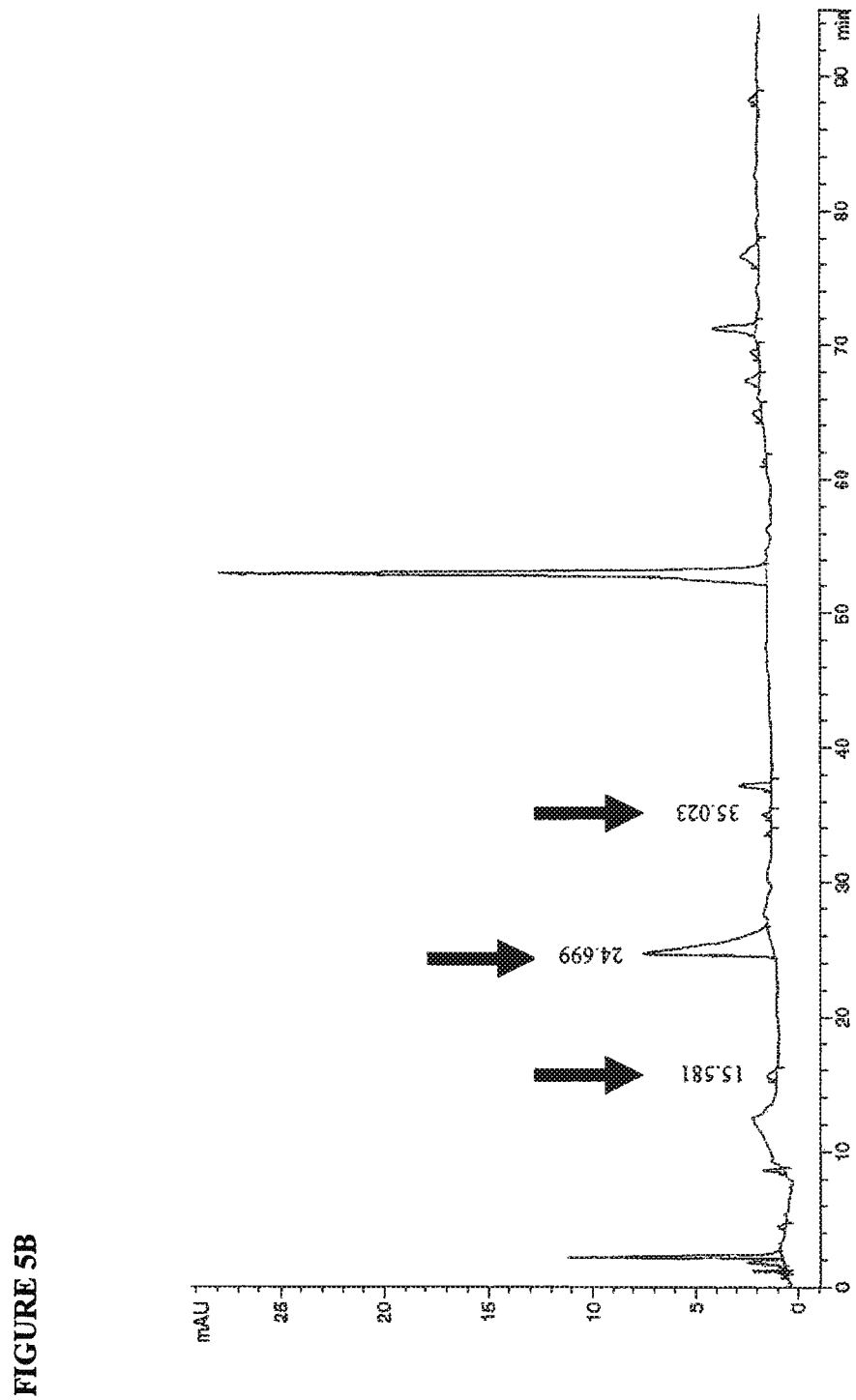

For the heparin entity of Example 1 comprising heparin and a core comprising colistin sulfate, the chromatogram of FIG. 5B exhibits at least 3 distinct peaks relative to the USP heparin chromatogram at 15.581, 24.699, and 35.023 minutes (shown by vertical arrows). Structurally, these new peaks are related to the core molecule colistin sulfate utilized in the construction of the heparin entity. When the heparin entity was depolymerized with heparinase-1, new structurally distinct polysaccharide units that contained the core molecule colistin sulfate were produced.

Figure 5C:
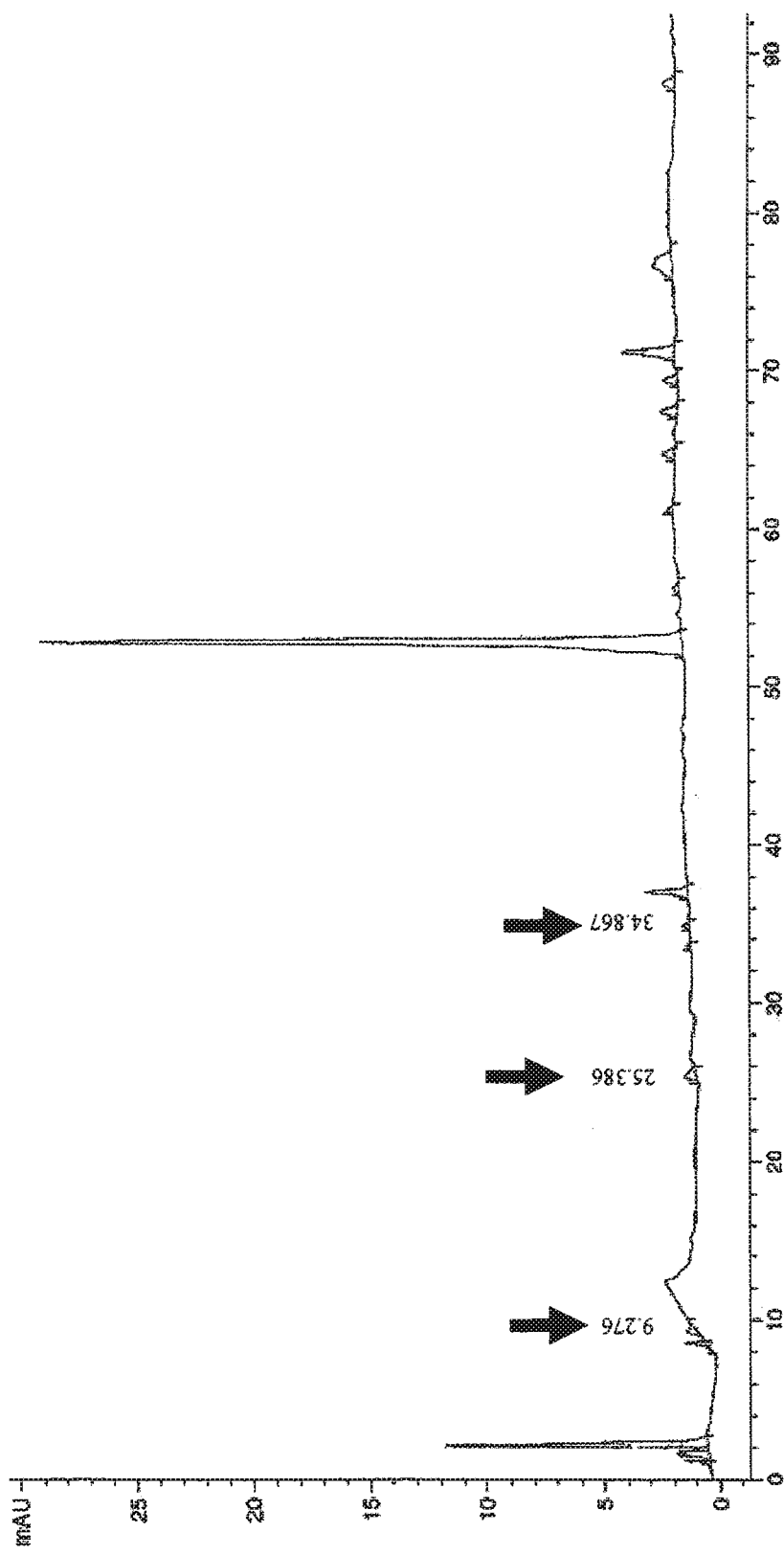

For the heparin entity of Example 2 comprising heparin and a core comprising neomycin sulfate, the chromatogram of FIG. 5C exhibits at least 3 distinct peaks relative to the USP heparin chromatogram at 8.276, 25.386, and 34.867 minutes (shown by vertical arrows). Structurally, these new peaks are related to the core molecule neomycin sulfate utilized in the construction of the heparin entity. When the heparin entity was depolymerized with heparinase-1, new structurally distinct polysaccharide units that contained the core molecule neomycin sulfate were produced.

Example 12

This example demonstrates a detection method for determining the composition of heparin entities immobilized on a surface using oligosaccharide mapping of heparinase-1 depolymerized heparin entities with strong anion exchange-high performance liquid chromatography (SAX-HPLC).

Heparin comprising free-terminal aldehydes was immobilized onto disks of ePTFE/PEI according to Example 9. The heparin entity of Example 1 was immobilized onto disks of ePTFE/PEI according to Example 7. Samples of approximately 4 cm$^2$ of each disk were placed in individual tubes. These samples were depolymerized to their constituent oligosaccharides by the addition of 1 ml of acetate buffer (consisting of 50 mM sodium acetate, 2.5 mM calcium acetate, pH 7.3) to each tube along with 60 µl of heparinase-1 solution. The heparinase-1 solution comprised acetate buffer (50 mM sodium acetate, 2.5 mM calcium acetate, pH 7.3) with heparinase-1 (EC 4.2.2.7, Sigma-Aldrich) at a concentration of 1.67 IU/ml. Tubes were incubated at 30° C. for 18 hours, and liquid samples of approximately 0.5 ml were taken and flash frozen at −85° C. for SAX-HPLC analysis as described in Example 11.

Figure 6A:
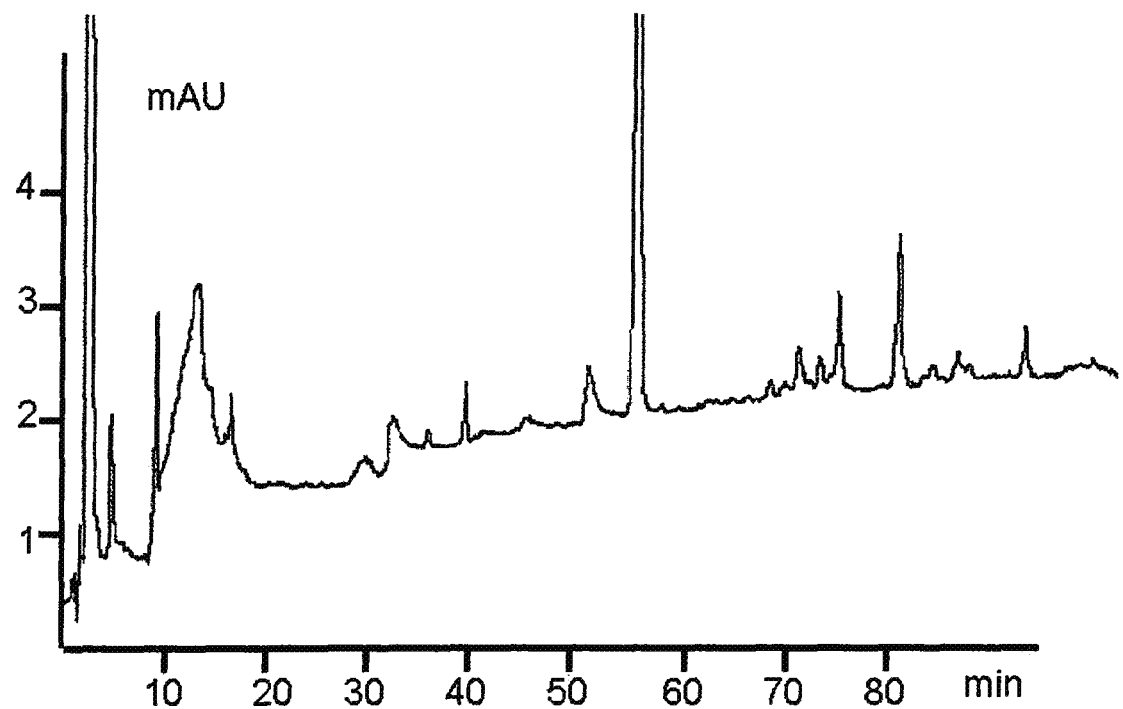
FIGS. 6 A and B depicts SAX-HPLC chromatograms from heparinase-1 depolymerization of ePTFE surface immobilized (a) USP heparin bound by free terminal aldehyde and (b) heparin entities constructed from heparin and colistin sulfate bound by free terminal aldehyde.
Figure 6B:
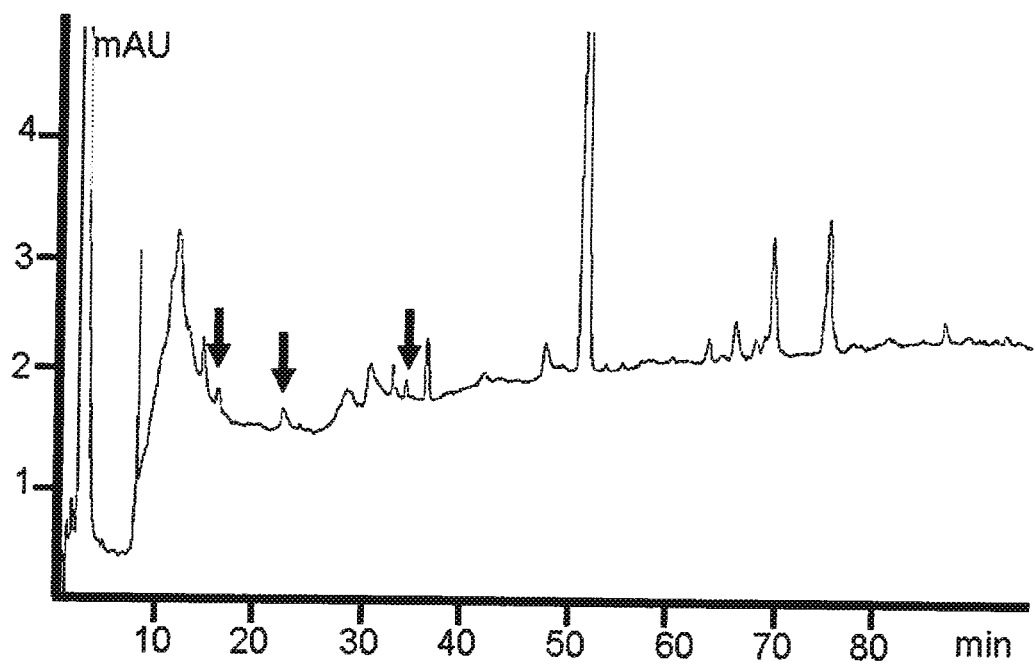

FIG. 6 shows the qualitative SAX-HPLC maps of surface depolymerized (A) heparin comprising free-terminal aldehydes immobilized on ePTFE and (B) a heparin entity constructed of heparin and a core of colistin sulfate immobilized on ePTFE. The chromatogram for heparin comprising free-terminal aldehydes immobilized on ePTFE was the base line case and served as a standard of reference for the heparin entity of Example 1. Each peak in FIG. 6A represents a unique oligosaccharide that is characteristic for heparin comprising free-terminal aldehydes immobilized on ePTFE. New peaks, as indicated by arrows in FIG. 6B, represent additional oligosaccharides units distinct from heparin comprising free-terminal aldehydes immobilized on ePTFE, and hence, identify the heparin entity of heparin and a core of colistin sulfate immobilized on ePTFE.

Example 13

This example describes the construction of a heparin entity comprising heparin and a core comprising poly-L-lysine.

This heparin entity does not contain free terminal aldehydes that can be used for attachment to a surface of a substrate. This heparin entity can be used for attachment to a surface of a substrate through ionic bonding.

Poly-L-lysine hydrobromide with molecular weight of 1,000 to 5,000 (0.1776 g, Sigma-Aldrich, St. Louis, Mo.) was dissolved in 300 ml of DI water containing MES buffer (pH 4.7, BupH™ Thermo Scientific) and pH adjusted to 4.7. To this was added, 10 g USP heparin, 4 g N-hydroxysulfosuccinimide (sulfo-NHS), and 4 g of EDC hydrochloride. The reaction was allowed to proceed at room temperature for 4 hours followed by dialysis overnight with 50,000 MWCO membrane (Spectra/Por®). The retentate was transferred to 50 ml tubes, flash frozen, and lyophilized to produce a fine powder. This powdered product was further used to immobilize the construct of heparin and a core of poly-L-lysine on an ePTFE sheet material through ionic bonding.

Example 14

The heparin entity of Example 13 was immobilized on the surface of the substrate ePTFE through ionic bonding.

Disks of ePTFE/PEI were prepared according to Example 7. The heparin entity of Example 13 containing a core of poly-L-lysine and no free terminal aldehydes, was attached, via ionic bonding, to the PEI layer(s) by placing 5 1×1 cm square ePTFE samples of the construction in a heparin entity-containing sodium chloride salt solution (approximately 0.247 g of heparin containing a core of poly-L-lysine containing no aldehydes, 0.16 g sodium citrate tri basic dehydrate, and 1.607 g NaCl dissolved in 55 ml DI water, pH 3.9) and kept for one hundred and twenty minutes (120 min) at 60° C.

The samples were then rinsed in DI water for 15 min, borate buffer solution (10.6 g boric acid, 2.7 g NaOH and 0.7 g NaCl dissolved in 1 L DI water, pH 9.0) for 20 min, and finally in DI water for 15 min followed by lyophilization of the entire construction to produce dry heparin bound to the ePTFE material. The presence and uniformity of the heparin containing a core of poly-L-lysine was determined by staining samples of the construction on both sides with toluidine blue. The staining produced an evenly stained surface indicating heparin was present and uniformly bound to the ePTFE material.

Example 15

This example demonstrates a detection method for determining the conjugation method for immobilizing heparin and heparin entities on a surface. Specifically, this example looks at the detection of surface-bonded unsaturated heparin fragments, or "nubs," on the surface of immobilized heparin or heparin entities after heparinase-1 depolymerization. Heparinase-1 depolymerization of heparin involves an enzymatic cleavage of heparin's non-reducing terminal uronic acid to a 4,5-unsaturated derivative that can react with various detection molecules, such as a thiol-terbium fluorescent molecule. A negative control of ionic bound heparin (Example 14) is included.

A thiol-terbium based florescent molecule was utilized. 5 grams hydroxypropyl β-cyclodextrin was dissolved into 50 ml DI-water, and 0.03894 grams terbium tris(4-methylthio) benzoate [Tb(4MTB$_3$)] was dissolved into 10 ml N,N-dimethylacetamide (DMAc). The Tb(4MTB$_3$) solution was then added drop wise into the hydroxypropyl β-cyclodextrin solution, yielding a clear colorless solution. The solution was then filtered through a 0.22 µm Sterix filter cartridge before use.

Samples of 1 cm×1 cm ePTFE coated substrates of Example 14, and 1 cm×1 cm samples of the heparin entity of Example 1, comprising heparin and a core comprising colistin sulfate, immobilized according to Example 7, were depolymerized with heparinase-1 before reaction with thiol-terbium. For comparison, heparin end-point aldehyde (made according to U.S. Pat. No. 4,613,665) immobilized onto PEI-ePTFE substrates in accordance with Example 7, was also utilized; this produced a surface in which the heparin was immobilized by end-point attachment.

Samples were depolymerized with 100 units heparinase-1 (EC 4.2.2.7, Sigma-Aldrich) diluted in 1 ml of buffer (20 mM tris, 50 mM NaCl, 10 mM CaCl$_2$, 0.01% BSA, and pH 7.5) for 35 min on a shaker at room temperature. This resulted in small fragment "nubs" of surface-bonded unsaturated heparin fragments bound to the surface of the ePTFE substrate. The samples were then rinsed in DI water for 15 min, borate buffer solution (10.6 g boric acid, 2.7 g NaOH and 0.7 g NaCl dissolved in 1 L DI water, pH 9.0) for 20 min, and stored in DI-water until used for final analysis. Fluorescence labeling of samples, through a Michael-like addition of the thiol-terbium compound to the unsaturated heparin fragment bound to the surface of the ePTFE substrate, was performed by placing each sample into vials containing Tb(4MTB$_3$)/hydroxypropyl β-cyclodextrin solution, purged with nitrogen for 1 minute, capped, and incubated overnight at 70° C. Samples were removed from vials, rinsed with 10 wt % hydroxypropyl β-cyclodextrin in DI-water, and placed on a glass microscope slide for imaging.

Imaging of samples was performed with a Nikon E-6000 microscope using an Ocean Optics Deuterium short-wavelength excitation source at an oblique angle. Both white light and UV excitation fluorescence images were taken using a FITC filter cube. All samples were maintained in a wet state during imaging to minimize background scattering, and imaged with a black and white camera. Samples excited with UV light were imaged, and green tinting was artificially added to the image for visualization purposes.

Distinct UV fluorescence, and hence the detection of surface-bonded unsaturated heparin fragments bound to the surface of the ePTFE substrate ("nubs"), was noted for the end-point aldehyde heparin and heparin entity comprising heparin and a core comprising colistin sulfate samples. An absence of UV fluorescence was noted for the macromolecular construct of ionically bound heparin and poly-L-lysine containing no aldehydes.

Example 16

This example describes the construction and utilization of an embodiment of the present invention in which high heparin anti-thrombin III (ATIII) binding is present for a heparin entity comprising heparin and a core comprising an amine-containing fluoropolymer. This heparin entity contains free terminal aldehydes that can be used for attachment to a surface of a substrate.

The amine-containing fluoropolymer was prepared using the following conditions. A copolymer comprising a mole ratio of 20:80 tetrafluoroethylene and vinyl acetate was prepared. To a nitrogen purged 1 L pressure reactor under vacuum were added 500 g DI water, 2 g of 20% aqueous ammonium perfluorooctanoate, 30 ml of distilled vinyl acetate, 10 g of n-butanol, and 0.2 g of ammonium persulfate. Tetrafluoroethylene monomer was then fed into the reactor until the reactor pressure reached 1500 KPa. The mixture was stirred and heated to 50° C. When a pressure drop was observed, 25 ml of vinyl acetate was slowly fed into the reactor. The reaction was stopped when the pressure dropped another 150 KPa after vinyl acetate addition. The copolymer was obtained from freeze-thaw coagulation of the latex emulsion and cleaned with methanol/water extraction. The copolymer then was hydrolyzed. To a 50 ml round bottle flask were add 0.5 g of the copolymer, 10 ml methanol and 0.46 g NaOH in 2 ml DI water. The mixture was stirred and heated to 60° C. for 5 hrs. The reaction mixture was then acidified to pH 4 and precipitated in DI water. The hydrolyzed copolymer was then acetalized. The hydrolyzed copolymer was dissolved in methanol at 2.5% w/v. To 50 g of this solution was added 33 ml of DI water with vortexing to produce a homogeneous solution. To this solution was added 0.153 g of aminobutyraldehyde dimethyl acetal, and 0.120 ml of a 37% HCl solution. The solution was reacted with stirring under nitrogen, 80° C., for 48 hrs. Sodium hydroxide from a 1M solution was added drop wise to a pH of about 9.0. The resulting copolymer of poly(tetrafluoroethylene-co-vinyl alcohol-co-vinyl[aminobutyraldehyde acetal]) (TFE-VOH-AcAm) was recovered by precipitation into copious DI water. The precipitate was filtered, redissolved into methanol, and reprecipitated into copious DI water for two more cycles. The final product was dried under vacuum at 60° C. for 3 hrs. FTIR and carbon NMR confirmed a polymer structure of poly(tetrafluoroethylene-co-vinyl alcohol-co-vinyl[aminobutyraldehyde acetal]).

48 mg of aldehyde-modified-heparin (made according to U.S. Pat. No. 4,613,665) was dissolved in 30 ml of DI water. To this solution was added 86 µl of 2.5% sodium cyanoborohydride solution (Aldrich) and the pH was adjusted to 3.8 with HCl. Separately, the TFE-VOH-AcAm copolymer was dissolved in superheated methanol at 2.5% w/v and then cooled to room temperature. To 20 ml of the TFE-VOH-AcAm solution was added 13 ml of the heparin solution drop wise, to produce a slightly milky emulsion. The emulsion was maintained at 60° C. for 2.5 hrs and then at room temperature for an additional 2 hrs. The emulsion was dialyzed against DI water using a 50 KDa membrane (SpectraPor) for 18 hrs, flash frozen at −80° C. and then lyophilized to a powder. 10 mg of the powder was suspended in 2.5 ml of ice cold DI water supplemented with 0.1 mg sodium nitrite (Sigma) and 20 µl of acetic acid (Baker). After reacting for 2 hrs at 0° C., the suspension was dialyzed against DI water using a 10 KDa membrane (SpectraPor) for 18 hrs, flash frozen at −80° C. and then lyophilized.

Example 17

This example describes the construction and utilization of an embodiment of the present invention in which high heparin ATIII binding is present for heparin entity comprising heparin and a core comprising an amine-containing fluoropolymer. This heparin entity contains aldehydes along the length of the heparin component that can be used for attachment to a surface of a substrate.

48 mg of aldehyde-modified-heparin (made according to U.S. Pat. No. 4,613,665) was dissolved in 30 ml of DI water. To this solution was added 86 µl of 2.5% sodium cyanoborohydride solution (Aldrich), and the pH adjusted to 3.8 with HCl. Separately, the TFE-VOH-AcAm copolymer of Example 16 was dissolved in superheated methanol at 2.5% w/v and then cooled to room temperature. To 20 ml of the TFE-VOH-AcAm solution was added 13 ml of the heparin solution drop wise to produce a slightly milky emulsion. The emulsion was maintained at 60° C. for 2.5 hrs and then at room temperature for an additional 2 hrs. The emulsion was dialyzed against DI water using a 50 KDa membrane (SpectraPor) for 18 hrs, flash frozen at −80° C. and then lyophilized to a powder.

A solution was prepared containing 100 ml DI water, 0.82 g sodium acetate, and 0.128 g sodium periodate (ICN). To 12 ml of this solution was suspended 12 mg of the powder. After reacting for 30 min in the dark, 1.2 ml of glycerol was added to quench the reaction, the suspension was dialyzed against DI water using a 10 KDa membrane (SpectaPor) for 18 hrs, flash frozen at −80° C. and then lyophilized.

Example 18

The heparin entities of Examples 16 and 17, comprising heparin and a core comprising amine-containing fluoropolymer, were immobilized onto the ePTFE/PEI substrates, following the method described in Example 7, except that the samples were not exposed to EtO. ATIII binding activity was measured following the method described in Example 7.

TABLE 3

| ATIII binding activity | | |
|---|---|---|
| Example # | Attachment type | pmol/cm2 |
| 16 | Free terminal aldehyde | 106 |
| 17 | Aldehyde along chain length (loop attachment) | 66 |

Example 19

This example describes the construction and utilization of an embodiment of the present invention in which high heparin ATIII binding is present for heparin entity comprising heparin and a core comprising an amine containing fluoropolymer. This heparin entity contains free terminal aldehydes that can be used for attachment to a surface of a substrate.

The amine containing fluoropolymer was prepared using the following conditions. A 4 L reactor was charged with 2 L of t-butanol. 50 g of tetrafluoroethylene (TFE), 200 g of perfluoromethylvinylether (PMVE) and 100 g of N-vinyl formamide (NFA) were added, along with 0.4 g of diisopropyl peroxydicarbonate as initiator. The solution was stirred at a speed of 800 rpm at 70° C. for 3 hrs. The precipitate was removed from the reactor, air-dried for 2 hrs, and dried at 40° C. under vacuum for 24 hrs. Proton and fluorine NMR analysis confirmed a TFE-PMVE-NFA polymer composition of 46 weight % NFA, 27 weight % PTFE and 27 weight % PMVE. This polymer was soluble in methanol and swelled in water.

25 g of the TFE-PMVE-NFA polymer was dispersed in 100 mL of DI water. The mixture was heated to 70° C., and 30 mL of 37% HCl was slowly added. The solution was kept at 90° C. for 4 hrs. Hydrolyzed polymer was recovered from acetone precipitation, air-dried for 2 hrs, and dried at 40° C. under vacuum for 24 hrs. FTIR analysis confirmed hydrolysis of the vinyl formamide groups to vinyl amine (VA) groups. The TFE-PMVE-VA polymer was water soluble.

In a vial, 2 g of USP Heparin was dissolved in 50 mL of 0.1M MES buffer, containing 0.8 g of EDC and 0.8 g sulfo-NHS. In a second vial, a second solution was prepared consisting of 1 g of TFE-PMVE-VA polymer and 30 mL of 0.1M MES buffer. The heparin solution was added drop wise into the polymer solution over 4 hrs at room temperature, and pH maintained at 4.7 with 1.0N NaOH. The reaction was kept overnight at room temperature. The solution was dialyzed in DI water for two days with 10,000 MWCO membrane (Spectra/Por®). The retentate was concentrated with rotary evaporation.

0.01 g NaNO2, 100 mL of DI water, and 2 mL of acetic acid were added to the retentate. The reaction proceeded at 0° C. for 2 hrs, followed by dialysis against DI water for two days, flash frozen at −80° C. and then lyophilized.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

The invention claimed is:

1. A medical substrate comprising:
a heparin entity bound onto a substrate via at least one heparin molecule, wherein said heparin entity comprises at least one heparin molecule and at least one core molecule, wherein said bound heparin entity is heparinase sensitive, and wherein said heparin molecule is bound to said substrate by one of: an end point attachment, a loop attachment, an end point aldehyde attachment, and an aldehyde attachment along the length of said heparin molecule.

2. The medical substrate of claim 1, wherein said substrate is selected from the group consisting of polyethylene, polyurethane, silicone, polyamide-containing polymers, polypropylene, polytetrafluoroethylene, expanded-polytetrafluoroethylene and biocompatible metals.

3. The medical substrate of claim 2, wherein said substrate is expanded-polytetrafluoroethylene.

4. The medical substrate of claim 2, wherein said biocompatible metal is Nitinol.

5. The medical substrate of claim 1, wherein said substrate is a component of a medical device.

6. The medical substrate of claim 5, wherein said medical device is selected from the group consisting of grafts, vascular grafts, stents, stent-grafts, bifurcated grafts, bifurcated stents, bifurcated stent-grafts, patches, plugs, drug delivery devices, catheters, cardiac leads, balloons and indwelling filters.

7. The medical substrate of claim 6, wherein said stents can be used in cardiac, peripheral or neurological applications.

8. The medical substrate of claim 6, wherein said stent-grafts can be used in cardiac, peripheral or neurological applications.

9. The medical substrate of claim 1, wherein said core molecule is either cyclic, linear, branched, dendritic, Y, T, or star shaped.

10. The medical substrate of claim 1, wherein said core molecule is selected from the group consisting of proteins, hydrocarbons, aminoglycosides, polysaccharides and polymers.

11. The medical substrate of claim 10, wherein said protein is selected from the group consisting of albumin, colistin and polylysine.

12. The medical substrate of claim 10, wherein said polysaccharide is selected from the group consisting of cyclodextrin, cellulose, and chitosan.

13. The medical substrate of claim 10, wherein said polymer is selected from the group consisting of polyethylene glycol (PEG) and co-polymers tetrafluoroethylene.

14. The medical substrate of claim 1, wherein said heparin is derived from bovine or porcine sources.

15. The medical substrate of claim 1, wherein after heparinase treatment heparin or fragments thereof will not be detected on said substrate.

16. The medical substrate of claim 1, wherein after heparinase treatment heparin or fragments thereof will be detected at a significantly lower level than before heparinase treatment on said substrate.

17. The medical substrate of claim 15, wherein heparin or fragments thereof are detected by a label that binds to heparin or fragments thereof.

18. The medical substrate of claim 17, wherein said label that binds to heparin or fragments thereof is selected from the group consisting of dyes, polyclonal antibodies, and proteins.

19. The medical substrate of claim 18, wherein said dye is toluidine blue.

20. The medical substrate of claim 1, wherein after heparinase treatment an insignificant amount of toluidine blue will bind to residual heparin or fragments thereof but will not be visually detected on said substrate.

21. The medical substrate of claim 1, wherein after heparinase treatment an insignificant amount of toluidine blue will bind to residual heparin or fragments thereof, and wherein detector readings will be about background levels or be insignificantly different from background when compared to a substrate without heparin entities.

* * * * *